US012146159B2

(12) United States Patent
Guillonneau et al.

(10) Patent No.: US 12,146,159 B2
(45) Date of Patent: *Nov. 19, 2024

(54) METHODS FOR OBTAINING REGULATORY T CELLS AND USES THEREOF

(71) Applicants: INSERM (INSTITUT NATIONAL DE LA SANTE ET DE LA RECHERCHE MEDICALE), Paris (FR); UNIVERSITE DE NANTES, Nantes (FR); CENTRE HOSPITALIER UNIVERSITAIRE DE NANTES, Nantes (FR)

(72) Inventors: Carole Guillonneau, Nantes (FR); Ignacio Anegon, Nantes (FR); Severine Bezie, Nantes (FR)

(73) Assignees: INSERM (INSTITUT NATIONAL DE LA SANTÉ ET DE LA RECHERCHE MÉDICALE), Paris (FR); NANTES UNIVERSITE, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 410 days.

This patent is subject to a terminal disclaimer.

(21) Appl. No.: 16/899,142

(22) Filed: Jun. 11, 2020

(65) Prior Publication Data
US 2020/0308543 A1 Oct. 1, 2020

Related U.S. Application Data

(62) Division of application No. 15/740,997, filed as application No. PCT/EP2016/065572 on Jul. 1, 2016, now Pat. No. 10,724,001.

(30) Foreign Application Priority Data

Jul. 3, 2015 (EP) ..................................... 15306092

(51) Int. Cl.
| C12N 5/0783 | (2010.01) |
| A61K 35/15 | (2015.01) |
| A61K 35/17 | (2015.01) |
| A61P 37/06 | (2006.01) |
| C12N 5/0786 | (2010.01) |

(52) U.S. Cl.
CPC .......... C12N 5/0637 (2013.01); A61K 35/15 (2013.01); A61K 35/17 (2013.01); A61P 37/06 (2018.01); C12N 5/0645 (2013.01); *C12N 2501/2334* (2013.01); *C12N 2501/599* (2013.01); *C12N 2502/1157* (2013.01)

(58) Field of Classification Search
None
See application file for complete search history.

(56) References Cited

U.S. PATENT DOCUMENTS

2009/0142317 A1 6/2009 Cao et al.
2013/0058963 A1* 3/2013 Maldonado ............... A61P 3/10
435/325

FOREIGN PATENT DOCUMENTS

| JP | 2011-505378 A | 2/2011 | |
| WO | WO-2004007701 A1 * | 1/2004 | ............. A61K 35/14 |
| WO | WO-2006050138 A2 * | 5/2006 | ......... A61K 39/0008 |
| WO | 2009/073599 A1 | 6/2009 | |
| WO | 2013/181438 A2 | 12/2013 | |
| WO | 2015/150492 A2 | 10/2015 | |
| WO | 2016/009041 A1 | 1/2016 | |

OTHER PUBLICATIONS

Bezie, Jul. 2014, Transplantation, vol. 98, p. 25.*
Needleman et al., "A General Method Applicable to the Search for Similarities in the Amino Acid Sequence of Two Proteins", Journal of Molecular Biology, 1970, pp. 443-453, vol. 48.
Nankivell et al., "The Natural History of Chronic Allograft Nephropathy", The New England Journal of Medicine, 2003, pp. 2326-2333, vol. 349, No. 24.
Srinivas et al., "Transplantation in 2011: New agents, new ideas and new hope", Nature Reviews Nephrology, 2012, pp. 74-75, vol. 8.
Londoño et al., "A Need for Biomarkers of Operational Tolerance in Liver and Kidney Transplantation", American Journal of Transplantation, 2012, pp. 1370-1377, vol. 12.
Wood et al., "Regulatory Immune Cells in Transplantation", Nature Reviews Immunology, 2012, pp. 417-430, vol. 12.
Niederkorn, "Emerging Concepts in CD8(+) T Regulatory Cells", Current Opinion in Immunology, 2008, pp. 327-331, vol. 20.
Picarda et al., "T-cell receptor specificity of CD8(+) Tregs in allotransplantation", Immunotherapy, 2011, pp. 35-37, vol. 3.
Guillonneau et al., "CD8+ regulatory T cells in solid organ transplantation", Current Opinion in Organ Transplantation, 2010, pp. 751-756, vol. 15.
Menoret et al., "Phenotypic and functional characterization of CD8(+) T regulatory cells", Methods in Molecular Biology, 2011, pp. 63-83, vol. 677.
Wei et al., "Functional overlap but differential expression of CSF-1 and IL-34 in their CSF-1 receptor-mediated regulation of myeloid cells", Journal of Leukocyte Biology, 2010, pp. 495-505, vol. 88.
Nandi et al., "Receptor-type Protein-tyrosine Phosphatase zeta is a Functional Receptor for Interleukin-34", The Journal of Biological Chemistry, 2013, pp. 21972-21986, vol. 288, No. 30.

(Continued)

*Primary Examiner* — Amy E Juedes
(74) *Attorney, Agent, or Firm* — NIXON & VANDERHYE

(57) ABSTRACT

Disclosed is a method for obtaining a population of human Treg cells including the steps of: (a) culturing a population of human monocytes with a medium including an amount of an interleukin-34 (IL-34) polypeptide in order to obtain a population of immunosuppressive macrophages; (b) co-culturing a population of human peripheral blood mononuclear cells (PBMCs) and the population of immunosuppressive macrophages obtained at step (a).

12 Claims, 14 Drawing Sheets

Figure 1:
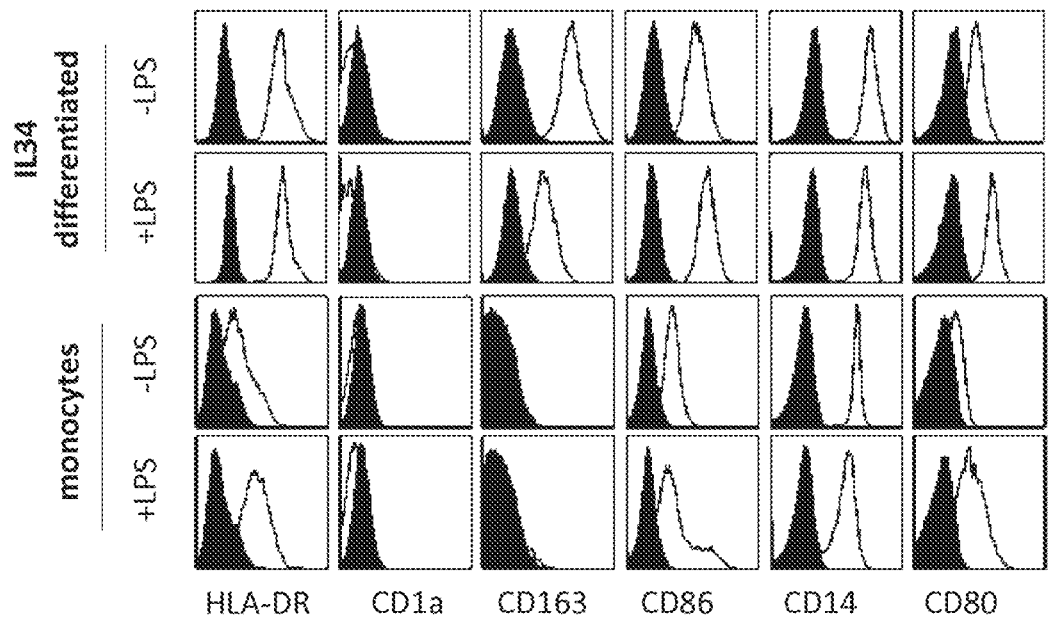

Specification includes a Sequence Listing.

(56) References Cited

OTHER PUBLICATIONS

Chihara et al., "IL-34 and M-CSF share the receptor Fms but are not identical in biological activity and signal activation", Cell Death and Differentiation, 2010, pp. 1917-1927, vol. 17.
Wang et al., "IL-34 is a tissue-restricted ligand of CSF1R required for the development of Langerhans cells and microglia", Nature Immunology, 2012, pp. 753-760, vol. 13, No. 8.
Bezie et al., "IL-34 is a Treg-specific cytokine and mediates transplant tolerance", The Journal of Clinical Investigation, 2015, pp. 3952-3964, vol. 125, No. 10.
Foucher et al., "IL-34- and M-CSF-induced macrophages switch memory T cells into Th17 cells via membrane IL-1alpha", European Journal of Immunology, 2015, pp. 1092-1102, vol. 45.
Ségaliny et al., "IL-34 and M-CSF form a novel heteromeric cytokine and regulate the M-CSF receptor activation and localization", Cytokine, 2015, pp. 170-181, vol. 76.
Foucher et al., IL-34 Induces the Differentiation of Human Monocytes into Immunosupressive Macrophages. Antagonistic effects of GM-CSF and IFNy, PLOS One, 2013, Article ID No. e56045, vol. 8, No. 2.
Melief et al., "Multipotent Stromal Cells Induce Human Regulatory T Cells Through a Novel Pathway Involving Skewing of Monocytes Toward Anti-inflammatory Macrophages", Stem Cells, 2013, pp. 1980-1991, vol. 31.
Ségaliny et al., "Interleukin-34 promotes tumor progression and metastatic process in osteosarcoma through Induction of angiogenesis and macrophage recruitment", International Journal of Cancer, 2015, pp. 73-85, vol. 137.
International Search Report, dated Sep. 9, 2016, from corresponding PCT application No. PCT/EP2016/065572.
Li et al., "Mechanism and localization of CD8 regulatory T cells in a heart transplant model of tolerance", Journal of Immunology, 2010, pp. 823-833, vol. 185, No. 2.
Guillonneau et al., "CD40lg treatment results in allograft acceptance mediated by CD8CD45RC T cells, IFN-gamma, and indoleamine 2,3-dioxygenase", Journal of Clinical Investigation, 2007, pp. 1096-1106, vol. 117, No. 4.
Savage et al., "Human Anti-Inflammatory Macrophages Induce Foxp3+GITR+CD25+ Regulatory T Cells, Which Suppress via Membrane-Bound TGFβ-1", The Journal of Immunology, 2008, pp. 2220-2226, vol. 181, No. 3.
Ordonez et al., "CD45RC Isoform Expression Identifies Functionally Distinct T Cell Subsets Differentially Distributed between Healthy Individuals and AAV Patients", PLOS one, 2009, Article ID No. e5287, vol. 4, No. 4.
Mahic et al., "Generation of highly suppressive adaptive CD8+CD25+FOXP3+ regulatory T cells by continuous antigen stimulation", European Journal of Immunology, 2008, pp. 640-646, Vo. 38.
Janikashvill et al., "Human monocyte-derived suppressor cells control graft-versus-host disease by inducing regulatory forkhead box protein 3-positive CD8+ T lymphocytes", Journal of Allergy and Clinical Immunology, 2015, pp. 1614-1624, vol. 135, No. 6.
Smith et al., "Revival of CD8+ Treg—mediated suppression", Trends Immunology, Jul. 2008, vol. 29, No. 7, pp. 337-342.

* cited by examiner

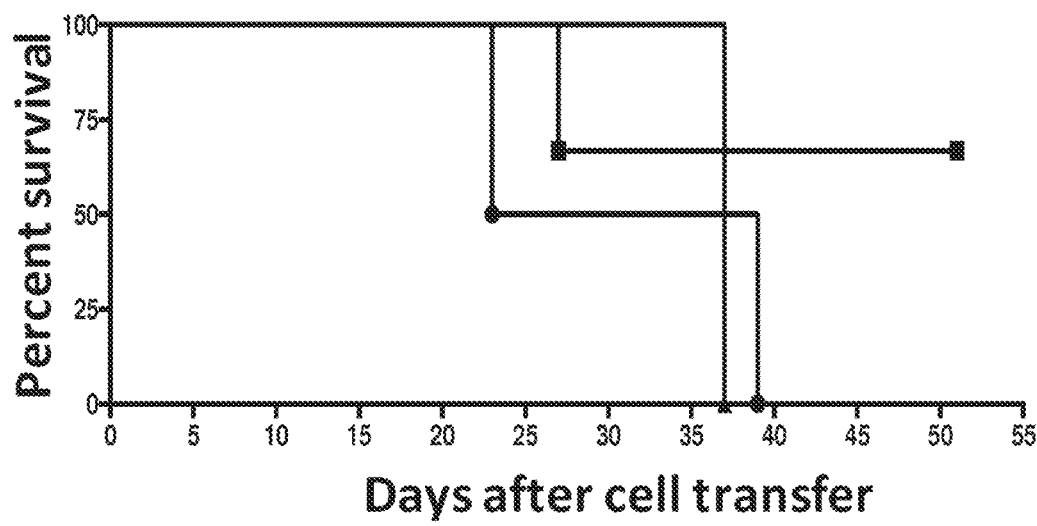

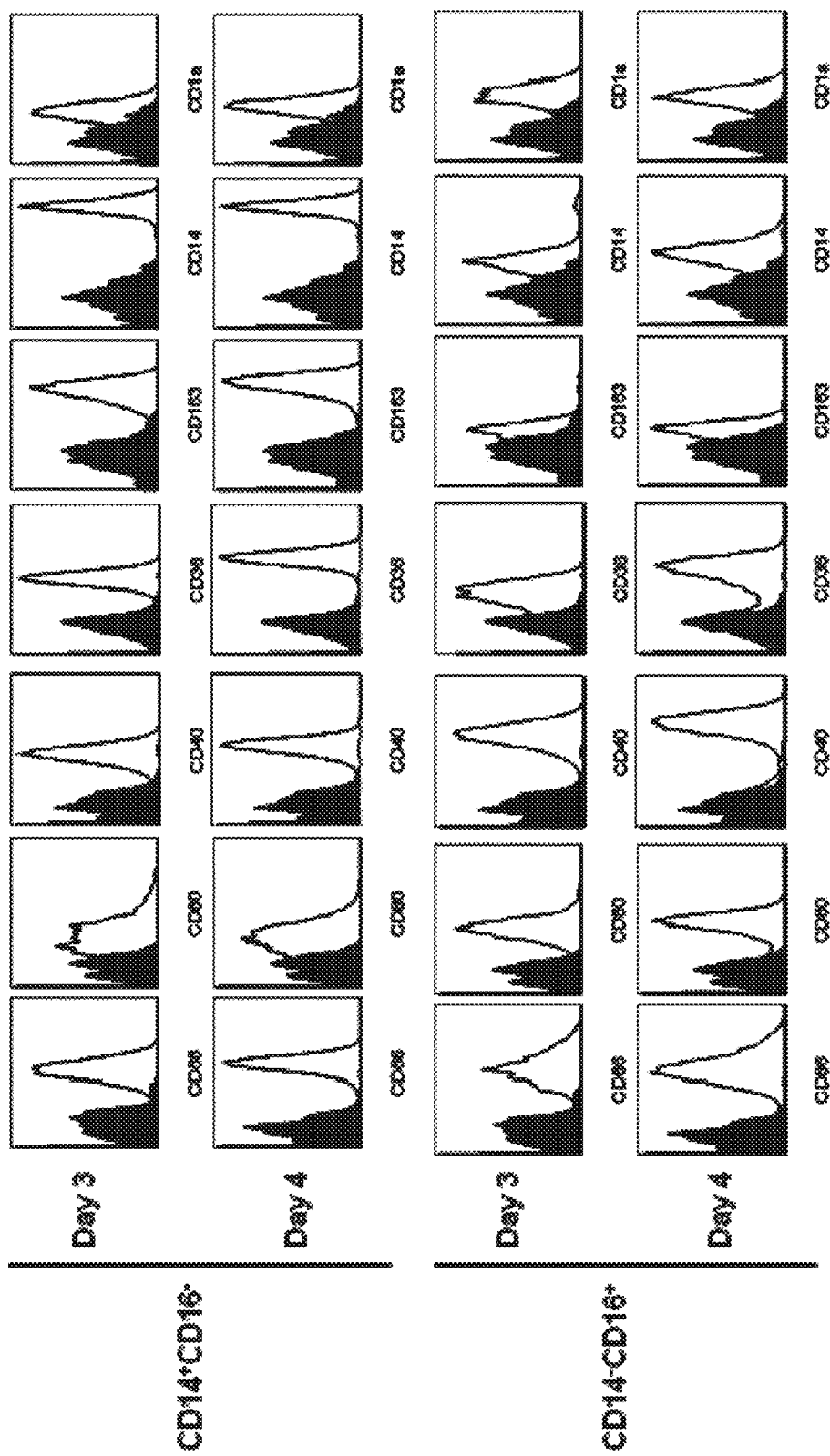

METHODS FOR OBTAINING REGULATORY T CELLS AND USES THEREOF

FIELD OF THE INVENTION

The invention is in the field of immunotherapy. More particularly, the invention relates to methods for obtaining a population of regulatory T cells.

BACKGROUND OF THE INVENTION

Regulatory T cells, or "Tregs" which encompass CD4+ and CD8+Foxp3+ Treg cells and CD45RC$^{low}$ Tregs are fundamental in controlling various immune responses in that Tregs can rapidly suppress the activity of other immune cells. In particular, Tregs are crucial for maintaining tolerance by downregulating undesired immune responses to self and non-self antigens. For instance, Treg defects have been discovered in patients with multiple sclerosis (MS), type I diabetes (T1D), psoriasis, myasthenia gravis (MG) and other autoimmune diseases. Similar links may also exist for atopy and allergic diseases. For all these diseases reports exist pointing to a reduced in vitro immune suppression of the patient's Treg cells. This has led to an increasing interest in the possibility of using Tregs in immunotherapy to treat or prevent autoimmune diseases, allergies and transplantation-related complications, such as graft rejection or graft-versus-host disease (GvHD).

For instance, organ transplantation has seen very significant improvements in both the prevention and treatment of acute rejection, but subclinical episodes and chronic graft dysfunction still heavily impact medium and long-term graft survival (1). Emerging therapeutic strategies, among them tolerance induction to donor antigens, are moving to the clinical stage after years of experimental model work (2, 3). Among natural mechanisms and tolerance inductive strategies, the use of different types of regulatory cells, including different types of CD4+ Tregs, are among the most promising ones (4). The uses of CD8$^+$ regulatory T cells (CD8$^+$ Tregs) have been highlighted in recent years by ourselves, and others, in the transplantation field, but also in other pathological situations (5-8).

Hence, there is a particular need for methods useful for generating and expanding Treg cells with high degree of purity, and simultaneously CD4$^+$ and CD8$^+$ Tregs, preferably without CD4$^+$ and CD8$^+$ effector T cells in order to obtain such a purified population of Treg cells which is particularly of interest in the fields of autoimmunity, allergy, transplantation, treatment with therapeutic protein and gene therapy, to avoid degradation of self or therapeutic molecules/tissues by the immune system.

Interleukin-34 (IL34) was identified in 2008 (9). Studies showed that IL34 shares homology with M-CSF and they act through a common receptor, CD115, also called CSF-1R, (9) expressed on the cell surface of monocytes, and in the brain through a newly described receptor, Receptor-type Protein-tyrosine Phosphatase ζ (PTP-ζ) (10). However, studies have demonstrated that IL34 and M-CSF display distinct biological activity and signal activation (11), in part due to their differing spatial and temporal expression (12). Up to now IL34 function has been mainly linked with the survival and function of monocytes and macrophages (osteoclasts, microglia) (12). IL34 protein expression in resting cells has been observed in keratinocytes, hair follicles, neurons, proximal renal tubule cells and seminiferous tubule germ cells (12), and also in heart, brain, lung, liver, kidney, spleen, thymus, testicles, ovaries, prostate, colon, small intestine, spleen red pulp and osteoclasts (9). So far, IL34 has not been linked to the effects on immune function of DCs or T cells (12).

More recently, IL34 was shown to induce the differentiation of human monocytes into immunosuppressive macrophages (also referred as IL34-Mφ) since said IL34-differenciated macrophages suppressed TCR-dependent T cell proliferation (13), to induce transplantation tolerance (13) and also to induce IL-17-producing effector T helper cells, called Th17 cells (14). However, IL34-differenciated macrophages have never been shown to be useful for generating and expanding Treg from peripheral blood mononuclear cells (PBMCs).

SUMMARY OF THE INVENTION

The present invention relates to methods for obtaining a population of regulatory T cells. In particular, the present invention is defined by the claims.

DETAILED DESCRIPTION OF THE INVENTION

The invention is based on results about a new efficient method for generating and expanding Treg from PBMCs without prior step of isolation of Tregs (usually 5% for Foxp3+ Tregs) contained in a biological sample obtained from a patient such as a blood sample. The inventors have indeed shown that human IL34-differentiated macrophages expand and potentiate human Tregs including human CD4+ and CD8+Foxp3$^+$ Tregs (above 60%) and CD4+ and CD8+ CD45RC$^{low}$ Tregs (near 100%). Moreover, the inventors have demonstrated that the IL34-expanded Tregs obtained by a method of the present invention displayed a highly potent suppressive capacity up to a 16:1 effector:suppressor ratio, comparatively to unstimulated and polyclonaly stimulated Tregs.

Methods for Obtaining A Population of Human Regulatory T Cells

Accordingly, the first aspect of the present invention relates to an in vitro/ex vivo method for obtaining of obtaining a population of human Treg cells comprising the steps of a) culturing a population of human monocytes with a medium comprising an amount of an interleukin-34 (IL-34) polypeptide in order to obtain a population of immunosuppressive macrophages (also named "IL34-differentiated macrophages"); and b) co-culturing a population of human peripheral blood mononuclear cells (PBMCs) and the population of immunosuppressive macrophages obtained at step (a).

In some embodiments, method comprises the steps of a) culturing a population of human monocytes with a medium comprising an amount of an interleukin-34 (IL-34) polypeptide in order to obtain a population of immunosuppressive macrophages; b) co-culturing a population of human peripheral blood mononuclear cells (PBMCs) and the population of immunosuppressive macrophages obtained at step (a) with a medium suitable for expanding the population of human Treg cells contained in the population of PBMCs; and c) optionally isolating the population of human Treg cells obtained at step (b).

In some embodiments, the method of the present invention comprises a step of isolating a population of human Treg cells from the population of PBMC prior to step (b). Therefore, according to this embodiment, step (b) comprises co-culturing a population of human Treg cells isolated from the population of PBMC and the population of immunosuppressive macrophages obtained at step (a).

In some embodiments, the method of the present invention comprises a step of isolating a population of human Treg cells after co-culture of step (b).

As used herein, the term "regulatory T cells" refers to T cells that suppress an abnormal or excessive immune response and play a role in immune tolerance. The regulatory T cells are typically "forkhead box P3 (Foxp3$^+$) regulatory T cells" and "CD45RC$^{low}$ cells". As used herein, the terms "forkhead box P3 (Foxp3$^+$) regulatory T cells" or "Foxp3$^+$ Treg cells" refer to 2-10% of CD4$^+$ and CD8$^+$ T cells in humans and rodents (rats or mice) whose the characteristic marker is the transcription factor Foxp3.

At step (a), the population of human monocytes that serve as starting material may be isolated according to any technique known in the art. For instance, the population of human monocytes may be obtained from various biological samples containing PBMC. Typically, they are isolated from peripheral blood. They may be isolated by positive selection with beads labelled with different ligands (eg, CD14). Such labelled cells may then be separated by various techniques such as cell sorting as described below.

In some embodiments, the population of human monocytes is thus a population of CD14$^+$ human monocytes. In some embodiments, the population of human monocytes is a population of CD14$^+$CD16$^+$ human monocytes. In some embodiments, the population of human monocytes is a population of CD14$^+$CD16$^-$ human monocytes.

As used herein, the term "medium" refers to a medium for maintaining a cell population, or culturing a cell population (e.g. "culture medium") containing nutrients that maintain cell viability and support proliferation. The medium may contain any of the following in an appropriate combination: salt(s), buffer(s), amino acids, glucose or other sugar(s), antibiotics, serum or serum replacement, and other components such as growth factors, cytokines etc. Media ordinarily used for particular cell types are known to those skilled in the art. The medium of the invention may be based on a commercially available medium such as RPMI 1640 from Invitrogen.

As used herein, the terms "Interleukin-34 polypeptide" or "IL-34 polypeptide" (Il-34) are well known in the art and refer to a cytokine that promotes the proliferation, survival and differentiation of monocytes and macrophages. The term includes naturally occurring IL-34 isoforms (e.g. Q6MP4 and Q6ZMJ4-2 with and without a Q81), variants and modified forms thereof. The naturally occurring human IL-34 protein has an amino acid sequence of 242 amino acids provided in the UniProt database under accession number Q6ZMJ4 and is shown as follows (SEQ ID NO: 1) or a polypeptide having a sequence at least 80%, 85%, 90%, 95%, 96%, 97%, 98% or 99% identical to the sequence SEQ ID NO: 1:

```
MPRGFTWLRYLGIFLGVALGNEPLEMWPLTQNEECTVTGFLRDKLQYRS

RLQYMKHYFPINYKISVPYEGVFRIANVTRLQRAQVSERELRYLWVLVS

LSATESVQDVLLEGHPSWKYLQEVETLLLNVQQGLTDVEVSPKVESVLS

LLNAPGPNLKLVRPKALLDNCFRVMELLYCSCCKQSSVLNWQDCEVPSP

QSCSPEPSLQYAATQLYPPPPWSPSSPPHSTGSVRPVRAQGEGLLP
```

As used herein, the term "polypeptide" refers to a polymer of amino acid residues joined by peptide bonds, whether produced naturally or synthetically, having no specific length. The term polypeptide does not exclude post-translational modifications that include but are not limited to phosphorylation, acetylation, glycosylation and the like. The term also applies to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "IL-34 polypeptide" is defined as including the naturally occurring human polypeptide IL-34 and naturally-occurring allelic variations of the polypeptide (e.g. variants rs8046424 and rs7206509). Allelic variations are naturally-occurring base changes in the species population which may or may not result in an amino acid change in a polypeptide or protein. Additionally, the IL-34 polypeptides according to the invention not only encompass polypeptides comprising or consisting of full-length IL-34 and variants thereof, but also polypeptides consisting of fragments thereof, provided the fragments are biologically active. Additionally included in this definition are both recombinant and synthetic versions of the polypeptide IL-34, which may contain induced modifications in the polypeptide and DNA sequences thereof. Accordingly, the term IL-34 polypeptide intends to encompass the functional equivalents of the IL-34 polypeptide encoded by the sequence SEQ ID NO: 1.

As used herein, a "functional equivalent" refers to a molecule (e.g. a recombinant polypeptide) that retains the biological activity and the specificity of the parent polypeptide. Therefore, the term "functional equivalent of the IL-34 polypeptide" includes variants and fragments of the polypeptide to which it refers (i.e. the IL-34 polypeptide) provided that the functional equivalents exhibit at least one, preferably all, of the biological activities of the reference polypeptide, as described below.

As used herein the term "polypeptide variant" refers to a biologically active polypeptide having at least about 80% amino acid sequence identity with the native sequence polypeptide. Such variants include, for instance, polypeptides wherein one or more amino acid residues are added, or deleted, at the N-or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid. In the frame of the application, the percentage of identity is calculated using a global alignment (i.e., the two sequences are compared over their entire length). Methods for comparing the identity and homology of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS: needle (global) program with a "Gap Open" parameter equal to 10.0, a "Gap Extend" parameter equal to 0.5, and a Blosum62 matrix. Polypeptides consisting of an amino acid sequence "at least 80%, 85%, 90%, 95%, 96%, 97%, 98% or 99% identical" to a reference sequence may comprise mutations such as deletions, insertions and/or substitutions compared to the reference sequence. The polypeptide consisting of an amino acid sequence at least 80%, 85%, 90%, 95%, 96%, 97%, 98% or 99% identical to a reference sequence may correspond to an allelic variant of the reference sequence. It may for example only comprise substitutions compared to the reference sequence. The substitutions preferably correspond to conservative substitutions as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

As used herein, a polypeptide "fragment" refers to a biologically active polypeptide that is shorter than a reference polypeptide (i.e. a fragment of the IL-34 polypeptide). Thus, the polypeptide according to the invention encompasses polypeptides comprising or consisting of fragments of IL-34, provided the fragments are biologically active.

In the frame of the invention, the biologically active fragment may for example comprise at least 175, 200, 205, 210, 215, 220, 225, 230, 235, 240 consecutive amino acids of the IL-34 polypeptide.

By "biological activity" of IL-34 or a functional equivalent thereof is meant the capacity to induce immunosuppressive macrophages (as described in the Section Examples. The skilled in the art can easily determine whether a functional equivalent of the IL-34 polypeptide is biologically active. To check whether the newly generated polypeptides induce immunosuppressive macrophages, a FACS analysis or a single cell gene expression profiling (see in Example section) may be performed for each polypeptide.

In some embodiments, the polypeptides of the invention may comprise a tag. A tag is an epitope-containing sequence which can be useful for the purification of the polypeptides. It is attached to by a variety of techniques such as affinity chromatography, for the localization of said polypeptide within a cell or a tissue sample using immunolabeling techniques, the detection of said polypeptide by immunoblotting etc. Examples of tags commonly employed in the art are the GST (glutathion-S-transferase)-tag, the FLAG™-tag, the Strep-Tag™, V5 tag, myc tag, His tag (which typically consists of six histidine residues), etc.

In some embodiments, the IL-34 polypeptide used in step (a) of the method of the present invention is a heterodimer IL-34/MCSF, as recently described (15).

In some embodiments, in step (a) of the method of the present invention, the population of human monocytes is cultured in presence of IL-34 and another cytokine, such as, for example, IL-4 or IL-10. In some embodiments, in step (a) of the method of the present invention, the population of human monocytes is cultured in presence of IL-34 and a growth factor, such as, for example, MCSF (macrophage colony-stimulating factor).

In some embodiments, IL-34 is a human interleukin-34 (hIL-34), preferably a recombinant human interleukin-34 (rhIL-34).

Typically, IL-34 is added to the medium at a concentration ranging from 1 to 500 ng/ml, preferably from 10 to 100 ng/ml, more preferably at 50 ng/ml.

Typically, IL-4 is added to the medium at a concentration ranging from 1 to 500 ng/ml, preferably from 10 to 100 ng/ml, more preferably at 20 ng/ml.

Typically, IL-10 is added to the medium at a concentration ranging from 1 to 500 ng/ml, preferably from 10 to 100 ng/ml, more preferably at 20 ng/ml.

Typically, MCSF is added to the medium at a concentration ranging from 1 to 500 ng/ml, preferably from 10 to 100 ng/ml, more preferably at 25 ng/ml.

The step (a) of culturing the population of human monocytes in a medium comprising an amount of IL-34 shall be carried out for the necessary time required for the obtention of a population of immunosuppressive macrophages (or IL34-differentiated macrophages).

Typically, the culture of human monocytes with a medium of interest shall be carried out for between at least 3 or 4 days and not more than 8 days, preferably 6 days. In some embodiments, the culture of human monocytes with a medium of interest is carried out for 3, 4, 5, 6, 7 or 8 days or more.

At step (b), the population of peripheral blood mononuclear cells (PBMCs) may be isolated by methods well known by the skilled man in the art (e.g. by density centrifugation such Ficoll-Paque™ density-gradient centrifugation).

As used herein, the term "expanding" refers to the process of converting and/or amplifying a given population of cells (e.g. immune cells such as T cells). Expansion of T cells is preferably performed by culturing a cell population comprising T cells in the presence of antigen-specific stimulating agent such as, for example, antigens, cells, antibodies, lectins, etc. Expansion may also require culture of T cells in the presence of a cytokine.

In some embodiments, the medium suitable for expanding Treg comprises an amount of at least one cytokine. Examples of cytokines that may be present in the medium suitable for expanding Treg include, but are not limited to, IL-15, IL-12, IL-4, IL-7, IL-2, IFNγ, IL-34 and proinflammatory cytokines (such as, for example, IL-1 (in particular IL-1β), IL-6 and TNFα).

In some embodiments, the medium suitable for expanding Treg comprises an amount of interleukin-2 (IL-2) and/or an amount of interleukin-15 (IL-15).

In some embodiments, the medium suitable for expanding Treg comprises an amount of interleukin-2 (IL-2) and an amount of interleukin-15 (IL-15).

In some embodiments, IL-2 is a human interleukin-2 (hIL-2), preferably a recombinant human interleukin-2 (rhIL-2). rhIL-2 is commercially available for pharmaceutical uses. Suitable commercial forms include, e.g. Proleukin®, a recombinant human IL-2 composition.

In some embodiments, IL-15 is a human interleukin-15 (hIL-15), preferably a recombinant human interleukin-15 (rhIL-15).

Typically, IL-2 is added to the culture medium of the invention at a concentration ranging from 1 to 250 ng/ml, preferably from 10 to 100 ng/ml, more preferably at 25 ng/ml. In some embodiments, IL-2 is added to the culture medium of the invention at a concentration ranging from 1 to 1000 U/ml, preferably from 10 to 500 U/ml, more preferably at 25 U/ml.

Typically, IL-15 is added to the culture medium of the invention at a concentration ranging from 1 to 100 ng/ml, preferably from 2.5 to 50 ng/ml, more preferably at 10 ng/ml.

Typically, IL-12 is added to the culture medium of the invention at a concentration ranging from 0.1 to 100 ng/ml, preferably from 1 to 50 ng/ml, more preferably at 5 ng/ml.

Typically, IL-4 is added to the culture medium of the invention at a concentration ranging from 0.1 to 100 ng/ml, preferably from 1 to 20 ng/ml, more preferably at 5 ng/ml.

Typically, IL-7 is added to the culture medium of the invention at a concentration ranging from 1 to 100 ng/ml, preferably from 2.5 to 50 ng/ml, more preferably at 10 ng/ml.

Typically, IFNγ is added to the culture medium of the invention at a concentration ranging from 1 to 500 ng/ml, preferably from 5 to 100 ng/ml, more preferably at 20 ng/ml.

Typically, IL-34 is added to the culture medium of the invention at a concentration ranging from 1 to 500 ng/ml, preferably from 10 to 100 ng/ml, more preferably at 50 ng/ml.

Typically, IL-1 is added to the culture medium of the invention at a concentration ranging from 1 to 100 ng/ml, preferably from 2.5 to 50 ng/ml, more preferably at 10 ng/ml.

Typically, IL-6 is added to the culture medium of the invention at a concentration ranging from 1 to 200 ng/ml, preferably from 5 to 100 ng/ml, more preferably at 20 ng/ml.

Typically, TNF is added to the culture medium of the invention at a concentration ranging from 1 to 200 ng/ml, preferably from 5 to 100 ng/ml, more preferably at 20 ng/ml.

Typically, TGFbeta is added to the culture medium of the invention at a concentration ranging from 0.01 to 100 ng/ml, preferably from 0.1 to 10 ng/ml, more preferably at 1 ng/ml.

The step (b) of co-culturing immunosuppressive macrophages (also called IL34-differentiated macrophages) and PBMCs in a medium suitable for expanding the population of human Treg cells contained in the population of PBMCs shall be carried out for the necessary time required for the expansion of Treg cells.

In some embodiments, PBMCs are allogenic to the immunosuppressive macrophages. As used herein, the term "allogeneic" refers to as being from the same species but to as different individuals having two different genetically Major Histocompatibility Complex (MHC) haplotypes. Thus, PBMCs may be isolated from a graft donor and the immunosuppressive macrophages may be isolated from the recipient. Alternatively, the PBMC may be isolated from a patient suffering from an autoimmune disease or allergy or from a patient in need of or waiting for an organ transplantation or from a bone marrow donor (such as, for example, for treating GVHD) or a healthy individual.

In some embodiments, PMBCs are syngeneic to the immunosuppressive macrophages. As used herein, the term "syngeneic" refers to genetically identical members of the same species.

Typically, the culture of PBMCs with a medium of interest shall be carried out for at least 12 days, such as, for example, between at least 12 days and not more than 20 days, or between at least 12 days and no more than 6 to 8 weeks, preferably 15 days. In some embodiments, the culture of PBMCs with a medium of interest is carried out for 12, 13, 14, 15, 16, 17, 18, 19, 20, 21, 22, 23, 24, 25, 26, 27, 28, 29, 30 or 31 days. In some embodiments, the culture of PBMCs with a medium of interest is carried out for 1 week, 2 weeks, 3, 4, 5, 6, 7, 8, 9 or 10 weeks or more.

In some embodiments, cytokines, preferably IL-2 and/or IL-15, are added to the culture medium of the invention at day 0 of culture of PBMCs. In some embodiments, cytokines, preferably IL-2 and/or IL-15, are further added to the culture medium of the invention once, twice or three or four times or more, for example at day 1, 2, 3, 4, 5, 6, 7, 8, 9, 10, 11, 12, 13, 14, 15, 16, 17, 18, 19 and/or 20. In some embodiments, cytokines, preferably IL-2 and/or IL-15, are added to the culture medium of the invention at day 0 and at day 5, 6, 7, 8 or 9 of culture of PBMCs, preferably at days 0 and 7. In some embodiments, cytokines, preferably IL-2 and/or IL-15 are added to the culture medium of the invention three times, preferably at day 0 and two additional times. In some embodiments, cytokines, preferably IL-2 and/or IL-15, are added to the culture medium of the invention four times, preferably at day 0 and three additional times. In some embodiments, cytokines, preferably IL-2 and/or IL-15, are added to the culture medium of the invention 5 times, preferably at day 0 and 4 additional times, such as, for example, at days 0, 6, 13, 16 and 18. In some embodiments, cytokines, preferably IL-2 and/or IL-15, are added at day 0 and every 2, 3 or 4 days until the end of the culture.

In some embodiments, the enriched population of Treg contains a percentage of human Treg cells that is at least twice the percentage of human Treg cells within the population of PBMCs before enrichment. In some embodiments, the enriched population of Treg contains a percentage of human Treg cells that is at least 2, 3, 4, 5, 6, 7, 8, 9 or 10 fold the percentage of human Treg cells within the population of PBMCs before enrichment.

In some embodiments, the invention relates to a method for obtaining a population of human Treg cells comprising the steps of a) culturing a population of human monocytes with a medium comprising an amount of IL-34 in order to obtain a population of immunosuppressive macrophages; b) co-culturing the population of immunosuppressive macrophages obtained at step (a) and a population of allogeneic PBMCs, preferably with a medium comprising an amount of IL15 and an amount of IL2; and c) optionally isolating the population of human Treg cells obtained at step (b).

In some embodiments, the invention relates to a method for obtaining a population of human Treg cells comprising the steps of a) culturing a population of human monocytes with a medium comprising an amount of IL-34 in order to obtain a population of immunosuppressive macrophages; b) co-culturing the population of immunosuppressive macrophages obtained at step (a) and a population of syngenic PBMCs, preferably with a medium comprising an amount of IL15 and an amount of IL2; and c) optionally isolating the population of human Treg cells obtained at step (b).

In some embodiments, the macrophages and the population of PBMC are syngenic, and the macrophages present an allogenic antigen.

After step (b), human Tregs including human Foxp3$^+$ Tregs (above 60%) and CD45RC$^{low}$ Tregs (near 100%) have been expanded. However, it may be useful to highly purify and isolate the population of human Treg cells or a subpopulation of said human Treg cells such as for instance CD4$^+$CD25$^{high}$CD127$^{low}$ Tregs or CD8$^+$CD45RC$^{low}$ Tregs.

At step (c), isolation of the population of human Treg cells may be carried out by a variety of methods for detecting a particular immune cell population available for a skilled artisan, including immunoselection techniques, such as high-throughput cell sorting using flow cytometric methods, affinity methods with antibodies labeled to magnetic beads, biodegradable beads, non-biodegradable beads, use of bispecific antibodies specific for IL34 and a CD protein (such as, for example, CD4, CD8, CD25, CD127 or CD45RC, PD1, GITR), use of bispecific antibodies specific for IL34, IFNγ, TGFβ and IL10, use of trispecific antibodies and combination of such methods.

As used herein, the term "flow cytometric methods" refers to a technique for counting cells of interest, by suspending them in a stream of fluid and passing them through an electronic detection apparatus. Flow cytometric methods allow simultaneous multiparametric analysis of the physical and/or chemical parameters of up to thousands of particles per second, such as fluorescent parameters. Modern flow cytometric instruments usually have multiple lasers and fluorescence detectors. A common variation of flow cytometric techniques is to physically sort particles based on their properties, so as to purify or detect populations of interest, using "fluorescence-activated cell sorting". As used herein, "fluorescence-activated cell sorting" (FACS) refers to a flow cytometric method for sorting a heterogeneous mixture of cells from a biological sample into two or more containers, one cell at a time, based upon the specific light scattering and fluorescent characteristics of each cell and provides fast, objective and quantitative recording of fluorescent signals from individual cells as well as physical separation of cells of particular interest. Accordingly, FACS can be used with the methods described herein to isolate CD4$^+$ Treg and CD8$^+$ Treg.

Alternatively, isolation for immune cell populations (e.g. human CD4$^+$Foxp3$^+$ Treg and human CD8$^+$Foxp3$^+$ Treg) can be performed using bead based sorting methods, such as magnetic beads. Using such methods, cells can be separated and isolated positively or negatively with respect to the particular cell-surface markers.

As defined herein, "positive selection" refers to techniques that result in the isolation and detection of cells expressing specific cell-surface markers, while "negative selection" refers techniques that result in the isolation and detection of cells not expressing specific cell-surface markers. In some embodiments, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select Treg (i.e. CD8$^+$CD45RC$^{low}$ T cells and CD4$^+$CD25$^{high}$CD127$^{low}$ T cells).

In some embodiments, the step of isolating the human Foxp3$^+$ Treg cells may be carried out by positive and negative selection based on at least one of the cell-surface markers selected from the group consisting of CD4, CD8, CD25, CD45RC and CD127 and/or on at least one cytokine expression, such as, for example, IL10 or IL34. This step of isolation may be carried out using antibodies, including monovalent or multivalent antibodies, such as, for example, bispecific or trispecific antibodies.

The invention further relates to a method for expanding human Treg cells comprising the steps of a) culturing a population of human monocytes with a medium comprising an amount of an interleukin-34 (IL-34) polypeptide in order to obtain a population of immunosuppressive macrophages (also called IL34-differentiated macrophages); b) co-culturing a population of Treg and the population of immunosuppressive macrophages obtained at step (a) with a medium suitable for expanding said population of human Treg cells; and c) optionally isolating the population of human Treg cells obtained at step (b).

In some embodiments, Treg cells or monocytes may be obtained from iPSC (induced pluripotent stem cells).

In some embodiments, the population of Treg is allogenic to the immunosuppressive macrophages. Thus, Tregs may be isolated from a graft donor and the immunosuppressive macrophages may be isolated from the recipient. Alternatively, Tregs may be isolated from a patient suffering from an autoimmune disease or allergy, or from a patient in need of or waiting for an organ transplantation or from a bone marrow donor (such as, for example, for treating GVHD) or a healthy individual. In some embodiments, Tregs are syngeneic to the immunosuppressive macrophages.

In some embodiments, the population of Treg is a population of CD4$^+$Foxp3$^+$ Treg and/or of CD8$^+$Foxp3$^+$ Treg. In some embodiments, the population of Treg is a population of CD4$^+$CD45RC$^{low}$ Treg and/or of CD8$^+$CD45RC$^{low}$ Treg.

Typically, the culture of Tregs shall be carried out for at least 12 days, such as, for example, for between 12 days and not more than 6-8 weeks, preferably 15 days. In some embodiments, the culture of PBMCs with a medium of interest is carried out for 12, 13, 14, 15, 16, 17, 18, 19, 20, 21, 22, 23, 24, 25, 26, 27, 28, 29, 30 or 31 days. In some embodiments, the culture of PBMCs with a medium of interest is carried out for 1 week, 2 weeks, 3, 4, 5, 6, 7, 8, 9 or 10 weeks or more.

In some embodiments, cytokines, preferably IL-2 and/or IL-15, are added to the culture medium at day 0 of culture of Tregs. In some embodiments, cytokines, preferably IL-2 and/or IL-15, are further added to the culture medium once, twice or three times or more, for example at day 1, 2, 3, 4, 5, 6, 7, 8, 9, 10, 11, 12, 13, 14, 15, 16, 17, 18, 19 and/or 20. In some embodiments, cytokines, preferably IL-2 and/or IL-15, are added to the culture medium at day 0 and at day 5, 6, 7, or 8 of culture of Tregs. In some embodiments, cytokines, preferably IL-2 and/or IL-15, are added to the culture medium at day 0 and every 2, 3 or 4 days until the end of the culture.

In some embodiments of the method of the present invention, antibodies anti-CD3 and/or antibodies anti-CD8 are added to the culture medium at day 0, 1, 2, 3, 4, 5, 6, 7, 8, 9, 10, 11, 12, 13, 14, 15, 16, 17, 18, 19 and/or 20 of culture of PBMC or Tregs, preferably at day 0 and/or at day 11, 12, 13, 14 and/or 15.

In some embodiments, 0.1 to 10 μg/ml, preferably 0.25 to 4 μg/ml, more preferably 1 μg/ml of anti-CD3 antibody and/or 0.1 to 10 μg/ml, preferably 0.25 to 4 μg/ml, more preferably 1 μg/ml of anti-CD28 antibody are added to the culture medium.

Use of IL34 According to the Invention

IL34-expanded Tregs obtained by a method of the present invention as described above display a highly potent suppressive capacity up to a 16:1 effector:suppressor ratio, comparatively to unstimulated and polyclonaly stimulated Tregs.

Accordingly, the second aspect of the present invention relates to the use of IL34 for increasing the suppressive capacity of a population of Tregs.

The invention also relates to the use of IL34 for obtaining an enriched population of Tregs from a population of PBMCs. The invention relates to the use of IL34 for generating and expanding a population of Tregs.

The invention further relates to the use of IL34 for obtaining a population of immunosuppressive macrophages (also called IL34-differentiated macrophages).

The invention also relates to the immunosuppressive macrophages (also called IL34-differentiated macrophages) for obtaining an enriched population of Tregs from a population of PBMCs. The invention relates to the use of immunosuppressive macrophages for generating and expanding a population of Tregs.

Populations of Treg Cells According to A Method of the Present Invention And Pharmaceutical Compositions Comprising Them The third aspect of the present invention relates to an isolated/enriched population of Treg cells obtainable by a method as defined above.

In some embodiments; said isolated population of Treg cells (IL34-expanded Tregs) display a highly potent suppressive capacity as detailed in the Section Examples below.

In some embodiments; said isolated population of Treg cells is an isolated population of Foxp3$^+$ and CD45RC$^{low}$ Treg cells.

In some embodiments, said isolated population of human Treg cells is an isolated population of CD4$^+$Foxp3$^+$ Treg cells and/or CD8$^+$Foxp3$^+$ Treg cells.

In some embodiments, said isolated population of human Treg cells is an isolated population of CD4$^+$CD45RC$^{low}$ Treg cells and/or CD8$^+$CD45RC$^{low}$ Treg cells.

Within the context of the invention, the isolated/enriched population of Treg cells may be then pulsed with an antigen of interest in order to achieve a population of antigen-specific Treg cells, said antigen being provided in an amount effective to "prime" the isolated population of Treg cells and thus obtain a population of Treg cells specific for said antigen.

Indeed such primed Treg cells are useful in the prevention or treatment of unwanted immune responses, such as those involved in autoimmune disorders, immune reactions to therapeutic proteins, graft rejection, GVHD and/or allergies.

As used herein, the term "treatment" refers both to therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an unwanted immune response if, after receiving a therapeutic amount of Treg cells according to the present invention, the patient shows observable and/or measurable reduction in or absence of one or more of the following: reduction in the number of pathogenic cells; reduction in the percent of total cells that are pathogenic; and/or relief to some extent, one or more of the symptoms associated with the specific disease or condition; reduced morbidity and mortality, and improvement in quality of life issues. The above parameters for assessing successful treatment and improvement in the disease are readily measurable by routine procedures familiar to a physician.

The present invention thus further relates to a method for treating or preventing an unwanted immune response, wherein said method comprises administering the isolated/enriched population of Treg cells to a subject in need thereof. Preferably, a therapeutically effective amount of Treg cells of the invention is administered to the subject.

As used herein, the term "therapeutically effective amount" means level or amount of Tregs that is aimed at, without causing significant negative or adverse side effects to the target, (1) delaying or preventing the onset of an unwanted immune response; (2) slowing down or stopping the progression, aggravation, or deterioration of one or more symptoms of an unwanted immune response; (3) bringing about ameliorations of the symptoms of an unwanted immune response; (4) reducing the severity or incidence of an unwanted immune response; or (5) curing an unwanted immune response. A therapeutically effective amount may be administered prior to the onset of an unwanted immune response, for a prophylactic or preventive action. Alternatively or additionally, the therapeutically effective amount may be administered after initiation of an unwanted immune response, for a therapeutic action.

In some embodiments, the method of the present invention is for treating or preventing an immune and/or inflammatory disease or condition. Examples of immune and/or inflammatory disease or conditions include, but are not limited to, inflammatory bowel disease (IBD), ulcerative colitis, Crohn's disease, intestinal inflammation linked to food allergy (e.g. milk protein allergy, hen egg allergy or peanut allergy) or intolerance, intestinal inflammation linked to celiac disease, rheumatoid arthritis, polychondritis, septic arthritis, spondyloarthropathies or ankylosing spondylitis, juvenile idiopathic arthritis (JIA), psoriatic arthritis and diseases associated with arthritis such as systemic lupus erythematous, Sjogren's syndrome, scleroderma, dermatomyosotis, polymyosotis, polymyalgia rheumatica, fibromyalgia, sarcoidosis, or vasculitis, type I diabetes mellitus or autoimmune insulitis, multiple sclerosis, amyotropic lateral sclerosis (ALS), Devic's disease or NMO (neuromyelitis optica), demyelinating diseases, Alzheimer' disease (AD), Parkinson's disease (PD), poliomyelitis, motor neuron disease, (MND) Optic neuritis, Transverse myelitis, chronic inflammatory demyelinating polyneuropathy, thyroiditis, gastritis, uveitis (including anterior uveitis (comprising iritis, iridiocyclitis, and anterior cylitis), intermediate uveitis (comprising pars planitis, posterior cyclitis, and hyalitis), posterior uveitis (comprising choroiditis, chorioretinitis, retinochoroiditis, retinitis, and neuroretinitis), panuveitis, acute uveitis, recurring uveitis and chronic uveitis), uveoretinitis, scleritis, retinal vasculitis, diffuse unilateral subacute neuroretinitis, sympathetic ophthalmia, Vogt-Koyanagi-Harada (VKH) syndrome, sarcoidosis-related retinitis, Behçet's-related retinitis, acute retinal pigment epitheliitis, orchitis, oophoritis, psoriasis, prostatitis, encephalomyelitis, vitiligo, graft rejection and GVHD.

Accordingly, populations of Treg cells specific for an antigen associated with the disease to be treated (pathogenic antigen) or specific of the graft may be obtained. Therefore, the antigen of interest is selected from the group consisting of auto-antigens, allo-antigens and allergens.

The invention also provides a pharmaceutical composition comprising the population of Treg cells according to the invention and at least one pharmaceutically acceptable excipient.

As used herein, the term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA The invention further provides a medicament comprising the population of Treg cells according to the invention.

The fourth aspect of the present invention relates to a population of immunosuppressive macrophage (also called IL34-differentiated macrophages) obtainable by step (a) of the method as defined above.

In some embodiments; said immunosuppressive macrophages display a highly potent capacity to induce Treg cells as detailed in the Section Examples below.

Therefore, in some embodiments of the invention, said immunosuppressive macrophages are useful in the prevention or treatment of unwanted immune responses, such as those involved in autoimmune disorders, immune reactions to therapeutic proteins, graft rejection, GVHD and/or allergies. Without willing to be bound by a theory, the Applicant suggests that administering said immunosuppressive macrophages to a patient may induce the expansion of Treg cells, thereby preventing or treating the unwanted immune response.

The present invention thus further relates to a method for treating or preventing an unwanted immune response, wherein said method comprises administering the population of immunosuppressive macrophages to a subject in need thereof. Preferably, a therapeutically effective amount of immunosuppressive macrophages is administered to the subject.

The invention also provides a pharmaceutical composition comprising the population of immunosuppressive macrophages according to the invention and at least one pharmaceutically acceptable excipient.

The invention also provides a medicament comprising the population of immunosuppressive macrophages according to the invention.

In some embodiments, the pharmaceutical composition or the medicament of the invention comprises immunosuppressive macrophages and Treg cells. Therefore, in some embodiments, for therapeutic use, the optional step (c) of the method of the present invention (isolating step) is not carried out.

The invention will be further illustrated by the following figures and examples. However, these examples and figures should not be interpreted in any way as limiting the scope of the present invention.

FIGURES

FIG. 1: Phenotype of IL34-differentiated macrophages. The phenotype of $CD14^+$ monocytes from healthy individuals was evaluated 6 days after purification and differentiation or not with IL34. Cells were recovered and stimulated or not 24 h with LPS and stained for the expression of several markers. One representative histogram from three independent experiments.

Figure 2A:
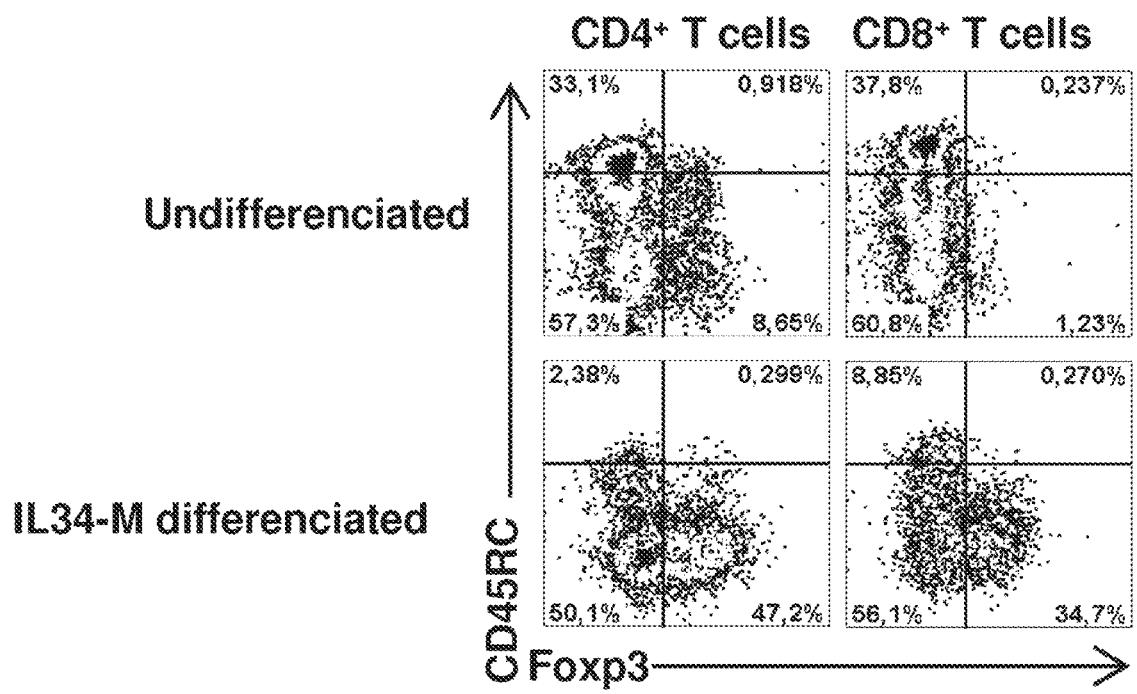
Figure 2B:
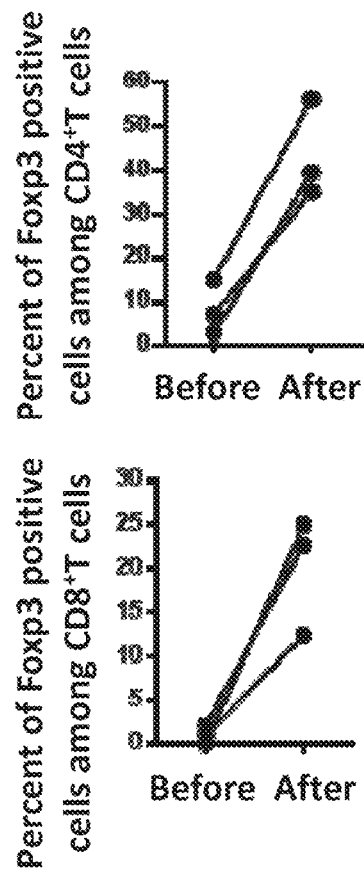
Figure 2C:
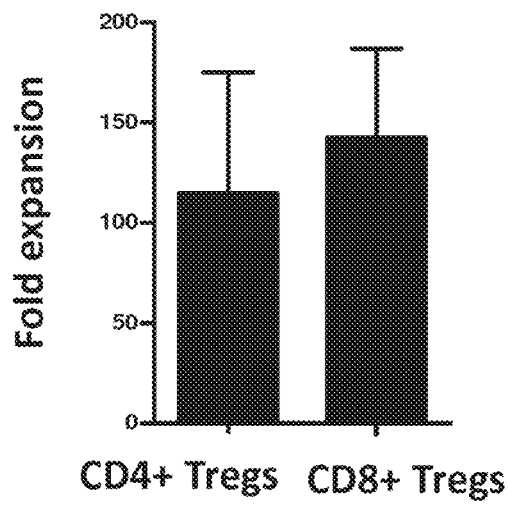
Figure 2D:
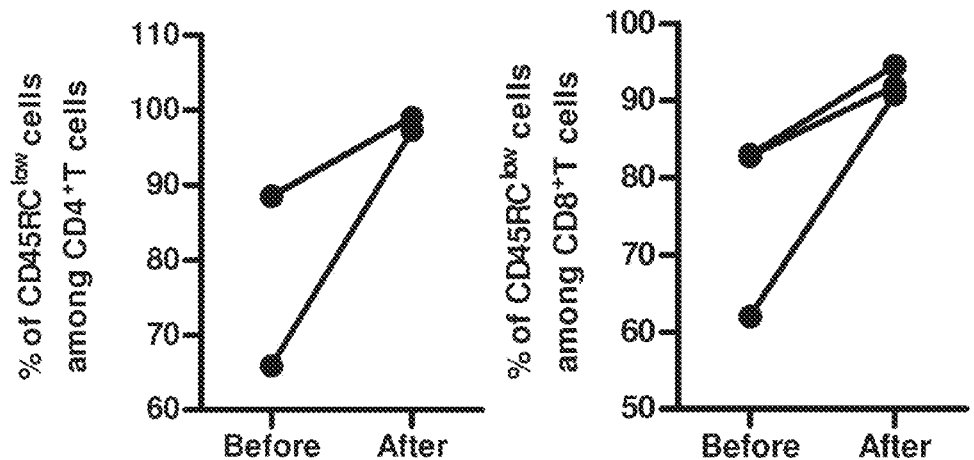
Figure 2E:
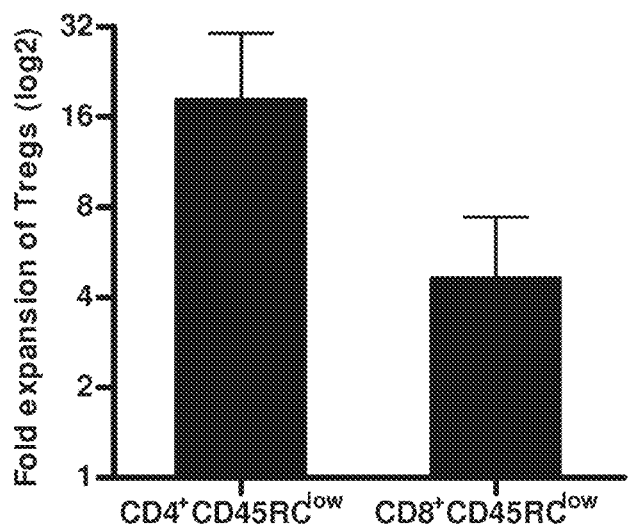
Figure 2F:
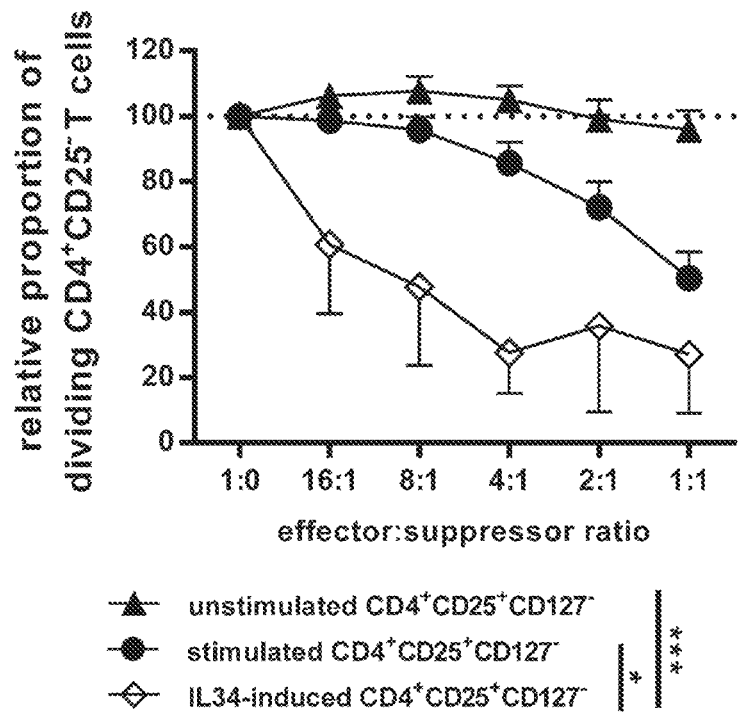
Figure 2G:
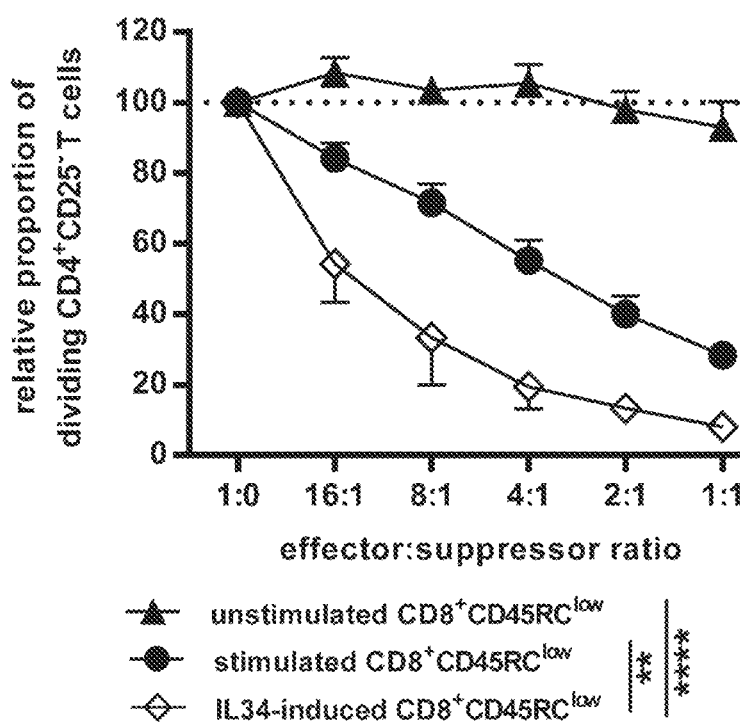
Figure 3A:
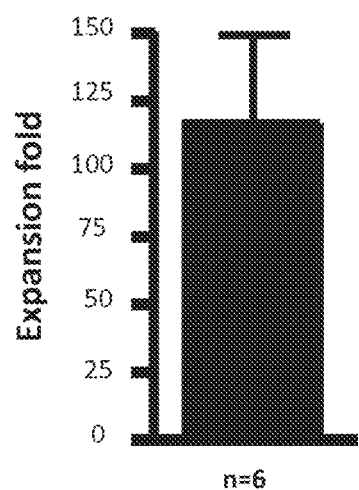
Figure 3B:
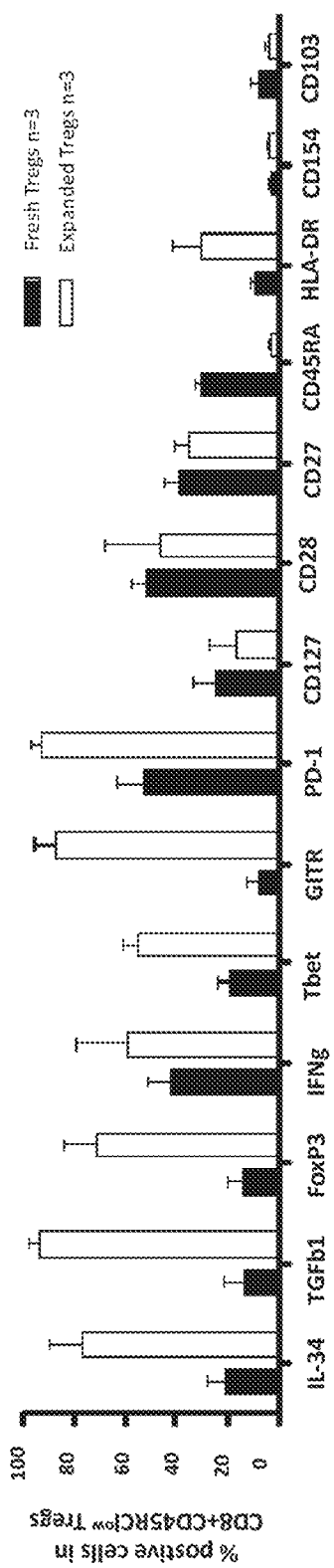

FIGS. 2A-2G: Efficient human $Foxp3^+$ Treg expansion and potentiation following IL34-macrophage differentiation. $CD14^+$ monocytes were differentiated for 6 days with IL34 or not and added to total allogeneic PBMCs for 15 days. The percentage of Foxp3 positive cells was evaluated in PBMCs among $CD4^+$ or $CD8^+CD45RC^{low}$ T cells. A representative plot (FIG. 2A) and graph (FIG. 2B) is shown before and after culture for 3 healthy individuals. (FIG. 2C) Fold expansion was evaluated for $Foxp3^+CD4^+$ or $CD8^+$ Tregs. (FIG. 2D) The percentage of $CD45RC^{low}$ evaluated among CD4 or CD8 T cells is shown before and after culture for 2 or 3 healthy individuals. (FIG. 2E) Fold expansion was evaluated for $CD45RC^{low}CD4^+$ or $CD8^+$ Tregs before and after culture for 3 healthy individuals. (FIGS. 2F-G) Unstimulated, stimulated or IL34-expanded $CD4^+CD25^{high}CD127^{low}$ and $CD8^+CD45RC^{low}$ Tregs were tested for suppression of CFSE-labeled $CD4^+CD25^-$ T cell proliferation in response to allogeneic T-depleted PBMCs and analyzed by flow cytometry for CFSE dilution after 5 days of culture. n=3. The proportion of dividing $CD4^+CD25^-$ T cells in the control proliferation condition with allogeneic T-depleted PBMCs only represented approximately 60% of the cells on day 5 and was given a value of 100 in each experiment. Results are expressed as mean±SEM of the relative proportion of dividing $CD4^+CD25^-$ T cells. A representative raw CFSE profile is displayed. Two Way RM ANOVA, *, $p<0.05$; , $p<0.01$; *, $p<0.001$; ****, $p<0.0001$ FIGS. 3A-3B: Expansion of $CD8^+$ Tregs with IL-34 differentiated macrophages. FIG. 3A. $CD8^+CD45RC^{low}$ Tregs were expanded around 115 fold in presence of IL34-differentiated macrophages. FIG. 3B. Co-culture of Tregs with IL34-differentiated macrophages resulted in enrichment in cells secreting suppressive cytokines IL34 and TGFb and expressing Tregs-associated markers Foxp3, GITR, PD1 and HLADR. Mean+/−SEM of cells expressing Tregs-associated markers among $CD8^+CD45RC^{low}$ cells.

Figure 4A:
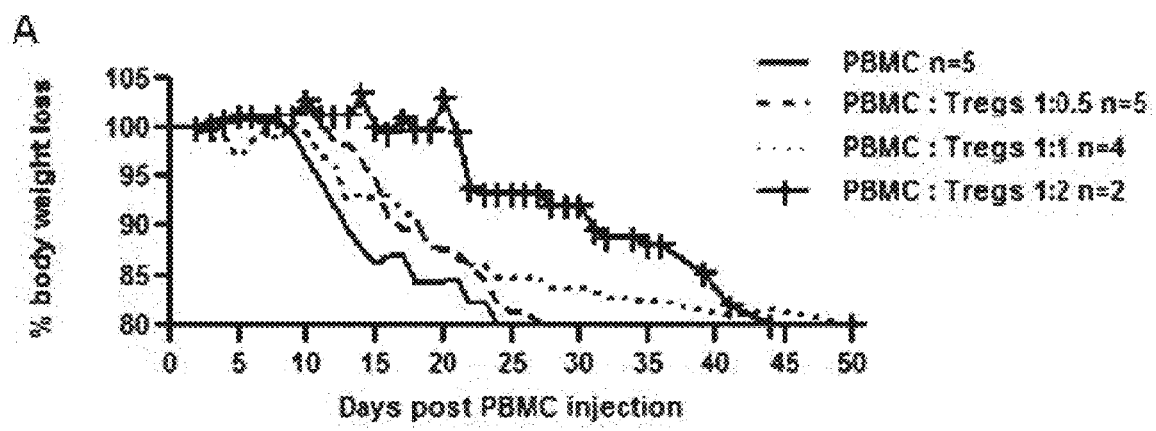
Figure 4B:
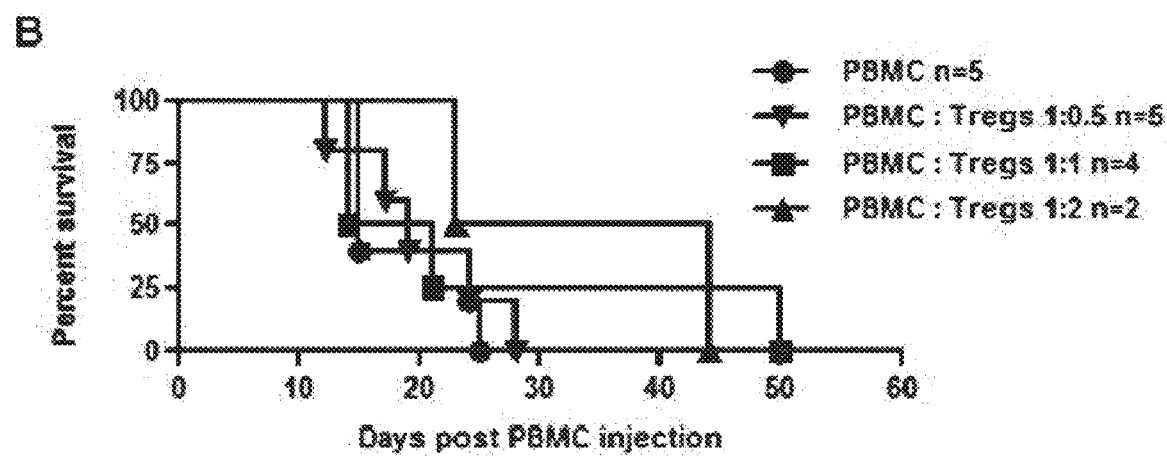

FIGS. 4A-4B: Effect of the Tregs of the invention on GVHD in humanized mice. FIG. 4A. Co-transfer of Tregs delayed mice weight loss induced by GVHD development in a dose dependent manner. FIG. 4B. Co-transfer of Tregs improved mice survival at ≥1:1 PBMC:Tregs ratios.

Figure 5A:
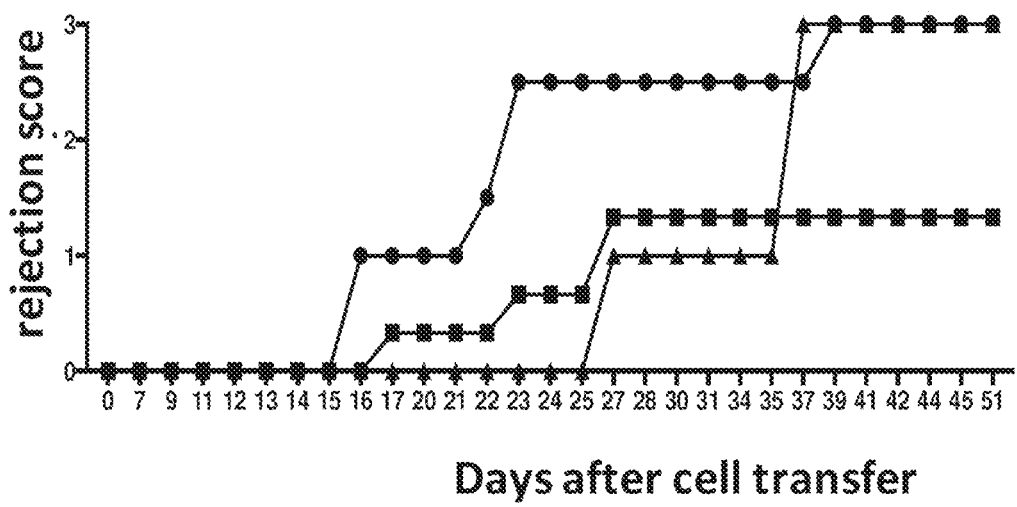

FIGS. 5A-5B: Effect of the Tregs of the invention on allogeneic skin graft rejection in humanized mice. FIG. 5A. Co-transfer of Tregs delayed rejection of allogeneic human skin graft in humanized mice. FIG. 5B. Graft survival was prolonged in humanized mice transferred with Tregs at a 1:2 PBMC:Tregs ratio.

Figure 6:
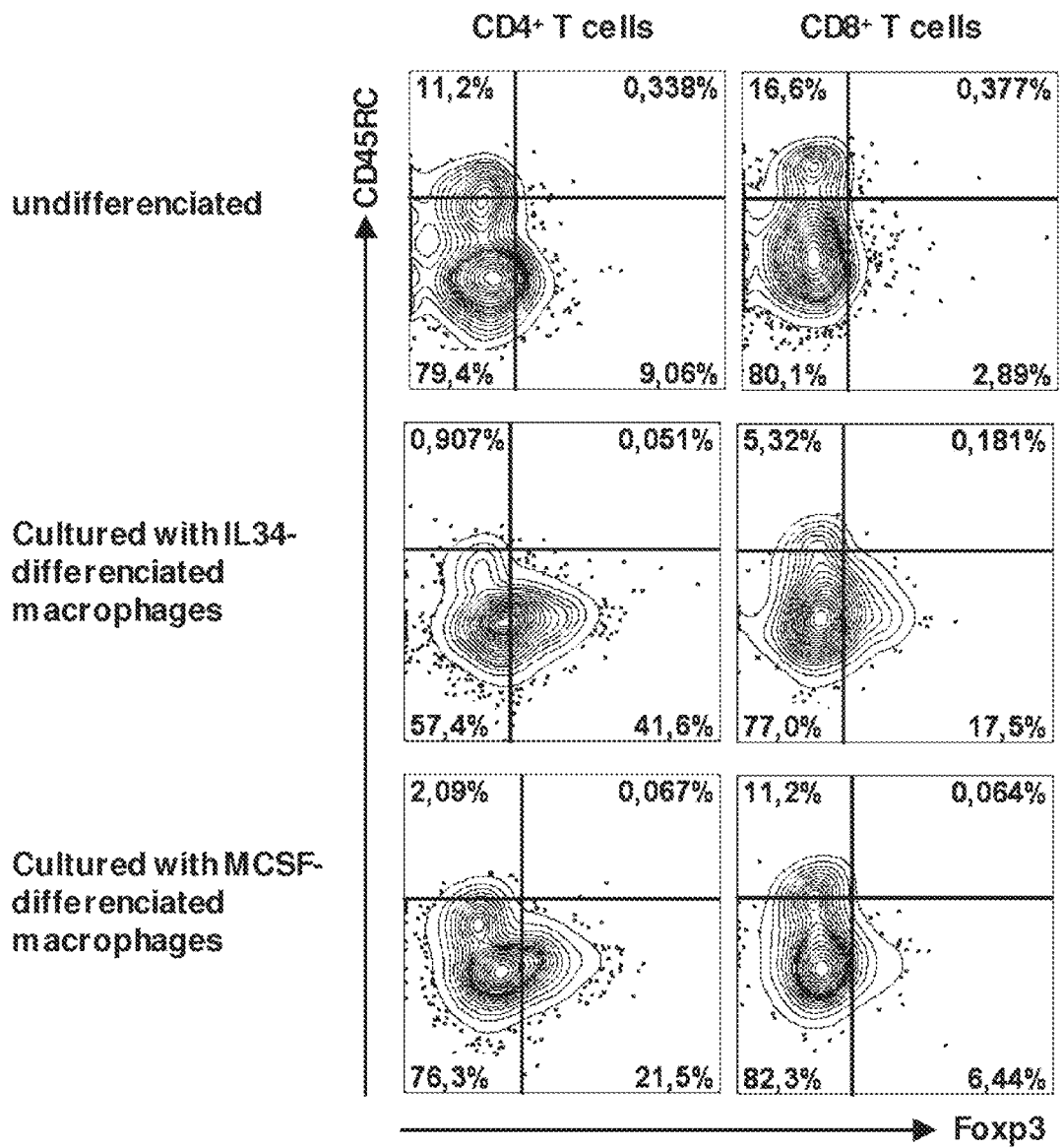

FIG. 6: Comparison of IL34-differentiated macrophages and MCSF-differentiated macrophages. The percentage of Foxp3 and CD45RC positive cells were evaluated in healthy individuals among $CD4^+$ or $CD8^+$ T cells following expansion with undifferenciated, IL34-differenciated or MCSF-differenciated macrophages. A representative plot of healthy individuals is shown.

Figure 7A:
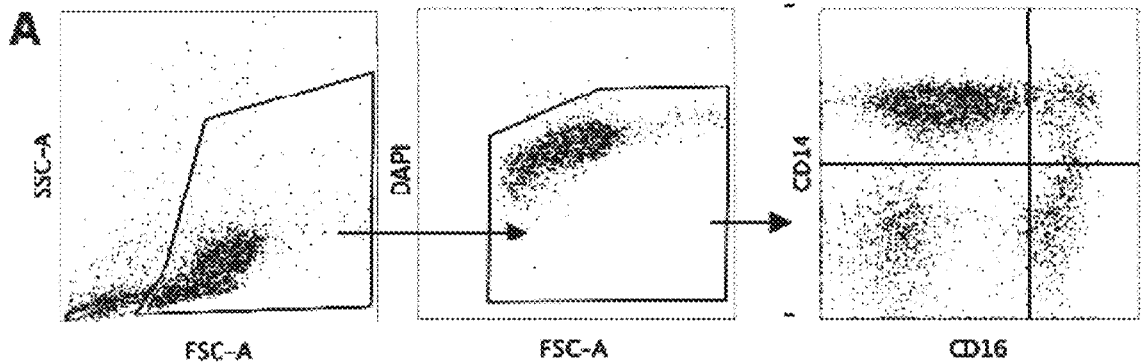
Figure 7B:
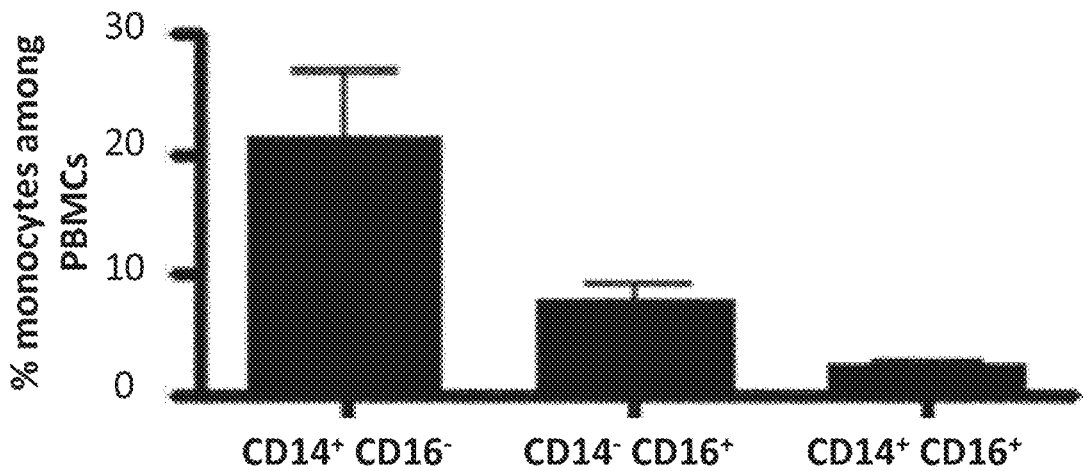
Figure 7C:
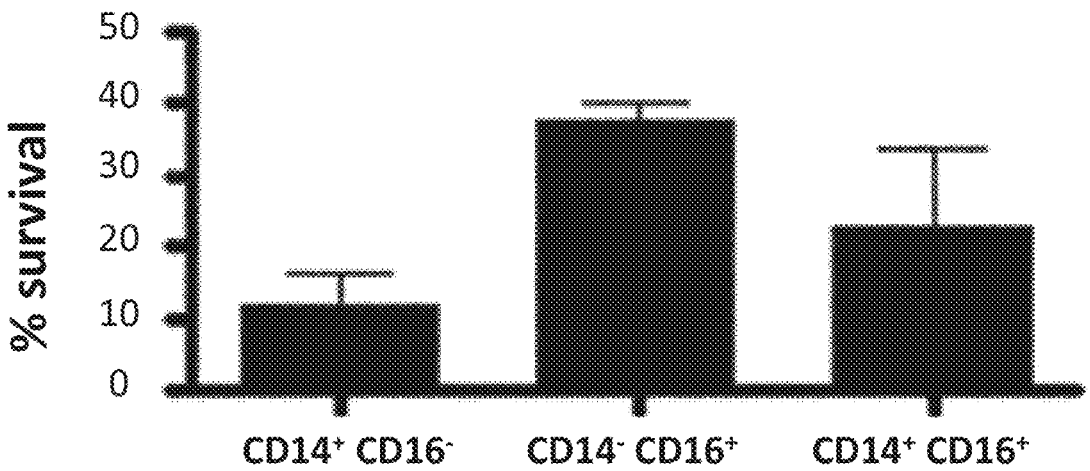
Figure 7D:
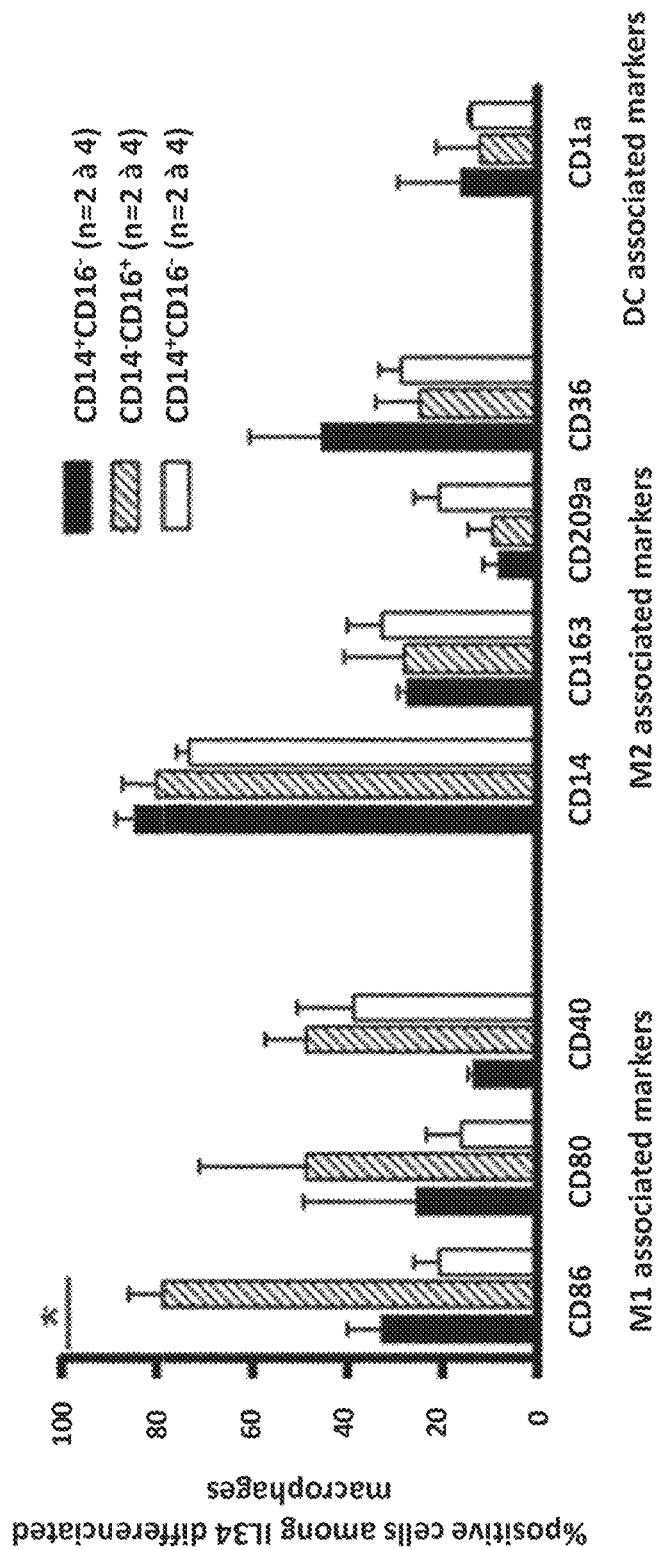

FIGS. 7A-7D: Effect of IL-34 on different subpopulations of monocytes. FIG. 7A. Monocytes were sorted on CD14 and CD16 markers expression by FACS Aria. FIG. 7B. Monocytes are mainly $CD14^+CD16^-$ in blood of healthy volunteers. $CD14^+CD16^-$, $CD14^-CD16^+$, and $CD14^+CD16^+$ represents 20%, 8% and 2.5% of PBMCs respectively. FIG. 7C. Cell survival in presence of IL34 depends on monocytes population. On day 6, 12%, 37% and 22% of seeded $CD14^+CD16^-$, $CD14^-CD16^+$, and $CD14^+CD16^+$ respectively were harvested. FIG. 7D. IL34 differentiation from both $CD14^+CD16^-$ and $CD14^+CD16^+$ monocytes resulted in higher number of M2-like macrophages with low expression of M1-associated markers than IL34 differentiation from $CD14^-$ monocytes ($CD14^-CD16^+$).

Figure 8A:
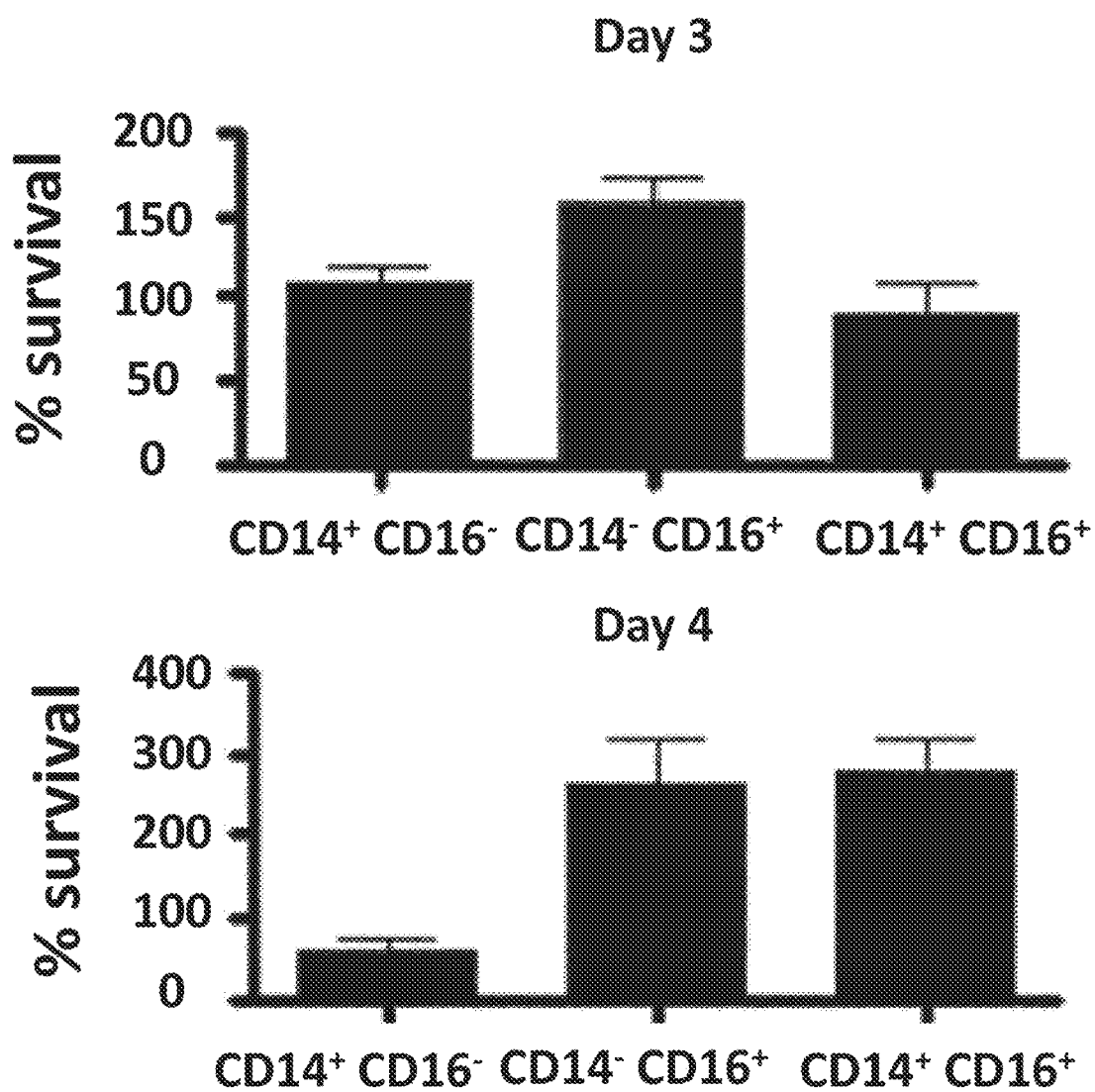
Figure 8B:
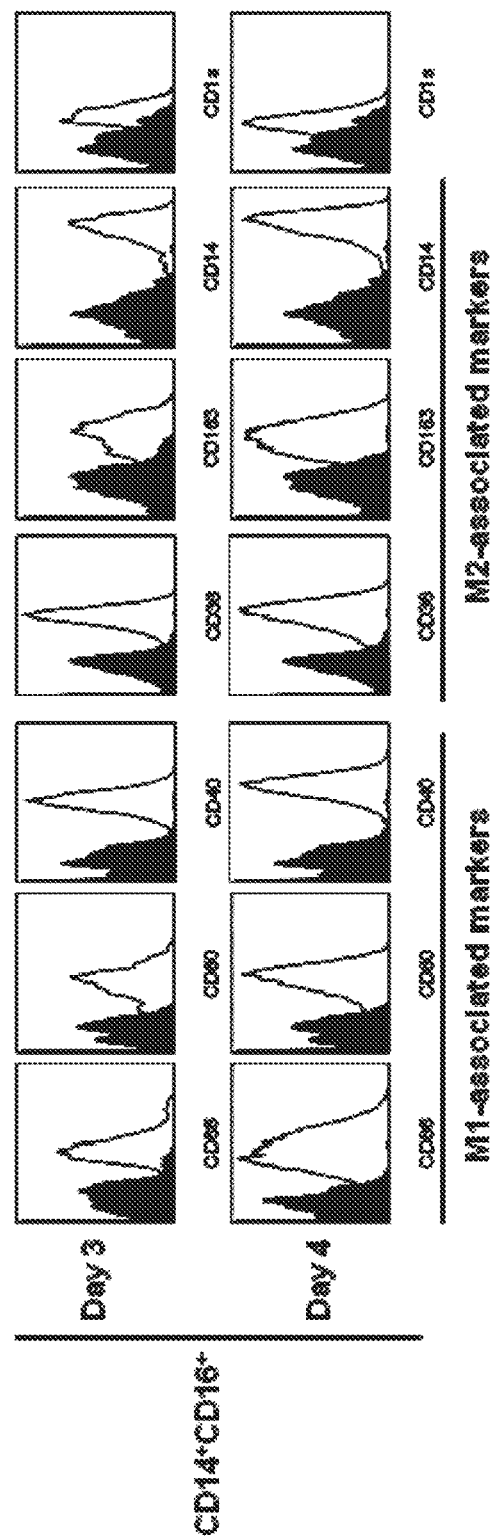

FIGS. 8A-8B: Effect of 3 days IL-34 treatment on macrophages. FIG. 8A. After 3 days culture with IL-34, 107%, 157% and 91% of seeded $CD14^+CD16^-$, $CD14^-CD16^+$, and $CD14^+CD16^+$ monocytes respectively were harvested. After 4 days culture with IL34, 59%, 264% and 275% of seeded $CD14^+CD16^-$, $CD14^-CD16^+$, and $CD14^+CD16^+$ monocytes respectively were harvested. FIG. 8B. IL34 differentiation from both $CD14^+CD16^-$ and $CD14^+CD16^+$ monocytes resulted in high expression of M2-associated markers and low expression of M1-associated markers as compared with IL34 differentiation from CD14⁻ monocytes (CD14⁻CD16⁺), after 3 or 4 days culture, as observed in 6 days culture.

EXAMPLE

Material & Methods

Healthy volunteer blood collection and PBMC separation: Blood was collected from healthy donors, after informed consent was given, at the Etablissement Français du Sang (Nantes, France). Blood was diluted 2-fold with PBS before PBMC were isolated by Ficoll-Paque density-gradient centrifugation (Eurobio) at 2000 rpm for 30 min at room temperature without braking. Collected PBMC were washed in 50 mL PBS at 1800 rpm for 10 min.

Graft-Versus-Host Disease And Skin Transplantation Rejection $1.5 \times 10^7$ PBMCs or FACS-Aria sorted CD45RC⁻ PBMCs from healthy volunteers (HV) donor were injected intravenously in 10-13 week old NSG SCID mice treated 16 hours earlier with whole-body sublethal irradiation of 1.5 Gy. Expanded Tregs were co-injected with syngeneic PBMCs in mice at a 1:1 or 1:2 PBMC:Tregs ratio. GVHD is characterized by mice weight loss; mice were sacrificed at 20% initial weight loss.

9 to 11 week old NSG mice were grafted with human skin. 6 weeks later, mice were i.v. injected with $1,5 \times 10^7$ PBMCs allogeneic to the skin to induce allograft rejection (day 0). Tregs syngeneic with PBMCs were expanded with IL34-differenciated macrophages as previously described and co-injected with PBMCs at 1:1 or 1:2 PBMC:Tregs ratio. Allograft rejection is scored from 1 to 3 by histological assessment.

Recipients were weighted every day and sacrificed when percentage of weight loss was ≥20% of their initial weight. Follow up was performed in blind conditions when possible. Groups of 3 to 6 animals were treated. Mice were matched in sex, age and initial weight and randomizely treated or not.

Treg and monocyte differentiation protocol: PBMCs from healthy volunteers (HV) blood were isolated by Ficoll gradient, and monocytes were elutriated according to FSC and SSC morphology parameters. CD14⁺ monocytes were then sorted by FACS Aria, washed, and seeded at $1 \times 10^6$/ml in medium (RPMI 1640, glutamine 2 mM, penicillin 100 U/ml, streptomycin 0.1 mg/ml, AB serum 10%) supplemented with 50 ng/ml hIL34 (ebiosciences). At day 6, cells were harvested, stimulated with 100 ng/ml LPS for 24 h for phenotype analysis, or seeded at $4 \times 10^5$/ml with 1 to 5 allogeneic PBMCs in Iscove medium (IMDM, glutamine 2 mM, penicillin 100 U/ml, streptomycin 0.1 mg/ml, AB serum 5%). IL-2 (25 U/ml) and IL-15 (10 ng/ml) were freshly added at days 10, 13 and 16. Macrophages were removed by successive transfers of floating cells to a new plate at days 19 and 21 for 48 h and 2 h respectively. At day 21, cells were stimulated with PMA and ionomycin in presence of brefeldin A for phenotype analysis, or T cells, CD8⁺CD45RC$^{low}$ T cells, and CD4⁺CD25$^{high}$CD127$^{low}$ T cells were sorted by FACS Aria for suppression assay. Fresh syngeneic CD4⁺CD25⁻ T cells were used as responder T cells stimulated with allogeneic APC isolated from the same donor as CD14⁺ cells. Proliferation was assessed 5 days later by CFSE dilution, by gating on CD3⁺CD4⁺ cells after exclusion of dapi-labeled dead cells and CPD405 labeled CD4⁺ Tregs.

Monoclonal antibodies and flow cytometry: Antibodies against CD3-PeCy7 (SKY7), CD4-PercPCy5.5 (L200), CD25-APCCy7 (M-A251), CD127-PE (HIL7-R M21, BD Bioscience), CD45RC-FITC (MT2, IQ Product), Foxp3-APC (236A/E7, ebiosciences) and IL34-PE (578416, R&D) were used to characterize human cell phenotypes. Fluorescence was measured with a Canto II cytometer (BD Biosciences, Mountain View, CA), and the FLOWJO software (Tree Star, Inc. USA) was used to analyze data. Cells were first gated by their morphology excluding dead cells by selecting DAPI viable cells.

CD14⁺ monocytes from healthy volunteers were cell-sorted and differentiated in the presence of IL34 for 6 days and the phenotype was analyzed for expression of CD163, CD14, HLA-DR, CD86 and CD80.

Results

IL34-Differentiated Macrophages Efficiently Induce Foxp3⁺CD45RC$^{low}$ Tregs and Potentiate Human CD4⁺CD25⁺CD127⁻ and CD8⁺CD45RC$^{low}$ Tregs.

CD14⁺ monocytes from healthy volunteers were cell-sorted and differentiated in the presence of IL34 for 6 days and the phenotype was analyzed (FIG. 1). We observed that IL34-differenciated macrophages expressed higher levels of CD163, CD14, HLA-DR, CD86 and CD80 than fresh monocytes. The differentiated macrophages were then added to allogeneic PBMCs for 15 days, then the proportion, number and suppressive capacity of Tregs were analyzed (FIG. 2). Interestingly, we observed that, following culture with IL34-differentiated macrophages, Foxp3⁺CD45RC$^{low}$CD4⁺ and Foxp3⁺CD45RC$^{low}$CD8⁺ T cells increased as a percentage of CD4⁺ or CD8⁺ T cells by 5 and 8.2 fold respectively (FIGS. 2A, 2B and 2D). This increase in percentage was also accompanied by an increase in the number of Foxp3⁺CD45RC$^{low}$CD4⁺ and Foxp3⁺CD45RC$^{low}$CD8⁺ T cells, by 83.4 and 100.6 fold respectively, as seen in the fold expansion (FIGS. 2B and 2C). Accordingly, we observed a significant increase in percentage and number of CD4+CD45RC$^{low}$ and CD8+CD45RClow Tregs (FIGS. 2D and 2E) Most importantly, we observed that the IL34-expanded CD4⁺CD25$^{high}$CD127$^{low}$ Tregs and CD8⁺CD45RC$^{low}$ Tregs displayed a highly potent suppressive capacity up to a 16:1 effector:suppressor ratio, with around 50% of the suppression compared to unstimulated and polyclonaly stimulated CD4⁺CD25$^{high}$CD127$^{low}$ Tregs and CD8⁺CD45RC$^{low}$ Tregs (FIGS. 2F and 2G).

Altogether, these results demonstrate that IL34-differenciated monocytes have the capacity to selectively expand and, not only to maintain, but potentiate Foxp3⁺CD45RC$^{low}$ Tregs suppressive capacity.

Expansion of CD8+ Tregs With IL-34-Differentiate Macrophages Improved Their Tolerogenic Profile Monocytes were isolated by Ficoll gradient, CD3⁺, CD19⁺ and CD16⁺ depletion and FACS Aria sorting on CD14 marker expression. CD14⁺ monocytes were seeded at $10^6$ cells/ml in complete medium (RPMI1640, 1% penicilline-stretpmycine, 1% glutamine, 10% FBS) supplemented with 50 ng/ml human IL34 protein and cultured for 6 days. On day 6, CD8⁺ Tregs were isolated from blood of a different HV (healthy volunteer) donor by Ficoll gradient, CD14⁺, CD16⁺ and CD19⁺ cells depletion and FACS Aria sorting on CD3, CD8 and CD45RC markers expression. CD3⁺CD8⁺CD45RC$^{low}$ cells were seeded at $10^6$ cells/ml in complete medium (RPMI1640, 1% penicilline-stretpmycine, 1% glutamine, 10% AB serum, 1% Hepes, 1% non essential amino acids, 1% sodium pyruvate) with allogeneic IL34-differenciated macrophages at 1:4 Tregs:monocytes ratio at day 0 and 1 µg/ml anti-CD3 and anti-CD28 Abs. On day 13, Tregs were stimulated again with 1 µg/ml anti-CD3 and anti-CD28. On days 6, 13, 16 and 18, culture medium was supplemented with 1000 U/ml human IL-2 and 10 ng/ml human IL-15. On day 20, Tregs were analyzed for expansion yield and were stimulated for 4 h with 50 ng/ml PMA and 1 µg/ml ionomycine in presence of 10 µg/ml Brefeldine A for Tregs associated markers expression analysis as compared to before expansion.

As shown in FIG. 3, IL-34-differentiated macrophages induce a 115 fold expansion of CD8+CD45RC$^{low}$ Tregs. Moreover, co-culture of Tregs with IL-34-differentiated macrophages induce an enrichment in cells secreting suppressive cytokines IL34 and TGFβ and expressing Tregs-associated markers Foxp3, GITR, PD1 and HLADR. Therefore, IL34-differentiated macrophages increased expression of Tregs-associated markers suggesting an increased suppressive activity for CD8$^+$CD45RC$^{low}$ Tregs.

CD8$^+$CD45RC$^{low}$ Tregs Expanded With IL34-Differentiated Macrophages Delayed Graft Versus Host Disease in Humanized Mice 10 to 13 week old NSG mice were 2Gy-irradiated 16 h before i.v. injection of 1,5×10$^7$ PBMCs to induce xenogeneic GVH reaction. CD8$^+$CD45RC$^{low}$ Tregs were sorted and expanded in presence of IL34-differentiated CD14$^+$ monocytes. Expanded Tregs were co-injected with syngeneic PBMCs in mice at a 1:1 or 1:2 PBMC:Tregs ratio. GVHD is characterized by mice weight loss; mice were sacrificed at 20% initial weight loss.

As shown in FIG. 4A, co-transfer of Tregs of the invention delayed mice weight loss induced by GVHD development in a dose dependant manner. Moreover, co-transfer of Tregs of the invention improved mice survival at ≥1:1 PBMC:Tregs ratios (FIG. 4B).

This result thus demonstrate that CD8$^+$CD45RC$^{low}$ Tregs expanded with IL34-differentiated macrophages efficiently delayed GVHD and can be used in cell therapy.

CD8$^+$CD45RC$^{low}$ Tregs Expanded With IL34-Differenciated Macrophages Delayed Allogeneic Skin Graft Rejection in Humanized Mice 9 to 11 week old NSG mice were grafted with human skin. 6 weeks later, mice were i.v. injected with 1,5×10$^7$ PBMCs allogeneic to the skin to induce allograft rejection (day 0). Tregs syngeneic with PBMCs were expanded with IL34-differenciated macrophages as previously described and co-injected with PBMCs at 1:1 or 1:2 PBMC:Tregs ratio. Allograft rejection is scored from 1 to 3 by histological assessment.

As shown in FIG. 5A, co-transfer of Tregs of the invention delayed rejection of allogeneic human skin graft in humanized mice. Moreover, graft survival was prolonged in humanized mice transferred with Tregs at a 1:2 PBMC:Tregs ratio (FIG. 5B).

This result thus demonstrate that Tregs expanded with IL34 differentiated macrophages can control alloimmune responses against the graft.

IL34-Differenciated Macrophages Are More Efficient Than MCSF-Differenciated Macrophages to Expand Foxp3$^+$ CD45RC$^{low}$ Tregs Monocytes were isolated from blood by Ficoll gradient, then CD3$^+$ and CD19$^+$ cells were depleted and FACS Aria sorted on CD14 marker expression. CD14$^+$ monocytes were seeded at 10$^6$ cells/ml in complete medium (RPMI1640, 1% penicilline-stretpmycine, 1% glutamine, 10% FBS) supplemented with 50 ng/ml human IL34 protein or 25 ng/ml human MCSF protein for 6 days. On day 6, macrophages were seeded at 4×10$^5$ cells/ml in complete medium (IMDM, 100 U/ml penicilline, 0.1 mg/ml stretpmycine, 2 mM glutamine, 5% AB serum) with allogeneic PBMCs at 5:1 PBMCs:macrophages ratio. 25 U/ml human IL2 and 10 ng/ml human IL15 were freshly added on days 10, 13 and 16. On day 21, T cells were stimulated for 4 h with 50 ng/ml PMA and 1 µg/ml ionomycine in presence of 10 µg/ml Brefeldine A for Foxp3 and CD45RC marker expression analysis.

Percentage of Foxp3 and CD45RC positive cells were evaluated in healthy individuals among CD4$^+$ or CD8$^+$ T cells following expansion with undifferenciated, IL34-differenciated or MCSF-differenciated macrophages. A representative plot of healthy individuals is shown in FIG. 6.

The obtained results show that IL34-differenciated macrophages are more efficient than MCSF-differenciated macrophages at expanding Tregs for cell therapy.

CD14$^-$CD16$^+$, CD14$^+$CD16$^-$ and CD14$^+$CD16$^+$ Behave Differently In Vitro in Presence of IL-34

Monocytes were isolated from blood by Ficoll gradient, CD3$^+$ and CD19$^+$ cells depletion and FACS Aria sorting on CD16 and CD14 markers expression. CD14$^+$CD16$^-$, CD14$^+$CD16$^+$ and CD14$^-$CD16$^+$ monocytes were seeded at 10$^6$ cells/ml in complete medium (RPMI1640, 1% penicilline-stretpmycine, 1% glutamine, 10% FBS) supplemented with 50 ng/ml human IL34 protein for 7 days. At day 7, cells were analyzed for macrophages associated markers expression as compared with M1 and M2 macrophages differentiated with 10 ng/ml GMCSF and 50 ng/ml IFNg or 25 ng/ml MCSF, 20 ng/ml IL4 and 20 ng/ml IL10 respectively.

As shown in FIG. 7, cell survival in presence of IL34 depends on monocytes population. On day 6, 12%, 37% and 22% of seeded CD14$^+$CD16$^-$, CD14$^-$CD16$^+$, and CD14$^+$CD16$^+$ respectively were harvested (see FIG. 7C). Moreover, as shown in FIG. 7D, IL34 differentiation from both CD14$^+$CD16$^-$ and CD14$^+$CD16$^+$ monocytes resulted in higher number of M2-like macrophages with low expression of M1-associated markers than IL34 differentiation from CD14$^-$ monocytes (CD14$^-$CD16$^+$).

Therefore, IL34 preferentially differentiate CD14+ monocytes towards M2-like cells.

Yield and Phenotype of 3 days IL34-Differenciated Macrophages

Monocytes were isolated from blood by Ficoll gradient, CD3$^+$ and CD19$^+$ cells depletion, and FACS Aria sorting on CD14 marker expression. CD14$^+$ monocytes were seeded at 10$^6$ cells/ml in complete medium (RPMI1640, 1% penicilline-stretpmycine, 1% glutamine, 10% FBS) supplemented with 50 ng/ml human IL34 protein and analyzed 3 days later for M1 and M2 associated markers expression.

Results are shown in FIG. 8. After 3 days culture with IL34, 107%, 157% and 91% of seeded CD14$^+$CD16$^-$, CD14$^-$CD16$^+$, and CD14$^+$CD16$^+$ monocytes respectively were harvested. After 4 days culture with IL34, 59%, 264% and 275% of seeded CD14$^+$CD16$^-$, CD14$^-$CD16$^+$, and CD14$^+$CD16$^+$ monocytes respectively were harvested. IL34 differentiation from both CD14$^+$CD16$^-$ and CD14$^+$CD16$^+$ monocytes resulted in high expression of M2-associated markers and low expression of M1-associated markers as compared with IL34 differentiation from CD14$^-$ monocytes (CD14$^-$CD16$^+$), after 3 or 4 days culture, as observed in 6 days culture.

These results demonstrate that 3 days culture of CD14$^+$ monocytes with IL34 are sufficient to induce a M2-like profile with a higher yield.

REFERENCES

Throughout this application, various references describe the state of the art to which this invention pertains. The disclosures of these references are hereby incorporated by reference into the present disclosure.

1. Nankivell, B. J., Borrows, R. J., Fung, C. L., O'Connell, P. J., Allen, R. D., and Chapman, J. R. 2003. The natural history of chronic allograft nephropathy. *N Engl J Med* 349:2326-2333.
2. Srinivas, T. R., and Kaplan, B. 2012. Transplantation in 2011: New agents, new ideas and new hope. *Nat Rev Nephrol* 8:74-75.
3. Londono, M. C., Danger, R., Giral, M., Soulillou, J. P., Sanchez-Fueyo, A., and Brouard, S. 2012. A need for biomarkers of operational tolerance in liver and kidney transplantation. *Am J Transplant* 12:1370-1377.
4. Wood, K. J., Bushell, A., and Hester, J. 2012. Regulatory immune cells in transplantation. *Nat Rev Immunol* 12:417-430.
5. Niederkorn, J. Y. 2008. Emerging concepts in CD8(+) T regulatory cells. *Curr Opin Immunol* 20:327-331.
6. Picarda, E., Anegon, I., and Guillonneau, C. 2011. T-cell receptor specificity of CD8(+) Tregs in allotransplantation. *Immunotherapy* 3:35-37.
7. Guillonneau, C., Picarda, E., and Anegon, I. 2010. CD8+ regulatory T cells in solid organ transplantation. *Curr Opin Organ Transplant* 15:751-756.
8. Menoret, S., Guillonneau, C., Bezie, S., Caron, L., Anegon, I., and Li, X. L. 2011. Phenotypic and functional characterization of CD8(+) T regulatory cells. *Methods Mol Biol* 677:63-83.
9. Wei, S., Nandi, S., Chitu, V., Yeung, Y. G., Yu, W., Huang, M., Williams, L. T., Lin, H., and Stanley, E. R. 2010. Functional overlap but differential expression of CSF-1 and IL-34 in their CSF-1 receptor-mediated regulation of myeloid cells. *J Leukoc Biol* 88:495-505.
10. Nandi, S., Cioce, M., Yeung, Y. G., Nieves, E., Tesfa, L., Lin, H., Hsu, A. W., Halenbeck, R., Cheng, H. Y., Gokhan, S., et al. 2013. Receptor-type protein-tyrosine phosphatase zeta is a functional receptor for interleukin-34. *JBiol Chem* 288:21972-21986.
11. Chihara, T., Suzu, S., Hassan, R., Chutiwitoonchai, N., Hiyoshi, M., Motoyoshi, K., Kimura, F., and Okada, S. 2010. IL-34 and M-CSF share the receptor Fms but are not identical in biological activity and signal activation. *Cell Death Differ* 17:1917-1927.
12. Wang, Y., Szretter, K. J., Vermi, W., Gilfillan, S., Rossini, C., Cella, M., Barrow, A. D., Diamond, M. S., and Colonna, M. 2012. IL-34 is a tissue-restricted ligand of CSF1R required for the development of Langerhans cells and microglia. *Nat Immunol* 13:753-760.
13. Bezie, S., Picarda, E., Ossart, J., Tesson, L., Usal, C., Renaudin, K., Anegon, I., and Guillonneau, C. 2015. IL-34 is a Treg-specific cytokine and mediates transplant tolerance. *J Clin Invest* 125:3952-3964.
14. Foucher, E. D., Blanchard, S., Preisser, L., Descamps, P., Ifrah, N., Delneste, Y., and Jeannin, P. 2015. IL-34- and M-CSF-induced macrophages switch memory T cells into Th17 cells via membrane IL-1alpha. *Eur J Immunol* 45:1092-1102.
15. Segaliny, A. I., Brion, R., Brulin, B., Maillasson, M., Charrier, C., Teletchea, S., and Heymann, D. 2015. IL-34 and M-CSF form a novel heteromeric cytokine and regulate the M-CSF receptor activation and localization. *Cytokine*.

---

The invention claimed is:

1. A method for treating an immune and/or inflammatory disease or condition in a subject, comprising obtaining a population of human CD8+ CD45RC$^{low}$ Treg cells by: (a) culturing a population of human monocytes in presence of interleukin-34 (IL-34) polypeptide in order to obtain a population of immunosuppressive macrophages; (b) co-culturing a population of human peripheral blood mononuclear cells (PBMCs) and the population of immunosuppressive macrophages obtained at step (a) to obtain a population of human CD8+ CD45RC$^{low}$ Treg cells; and (c) optionally isolating the human CD8+ CD45RC$^{low}$ Treg cells from the population obtained at step (b); and administering said population or said isolated population of human CD8+ CD45RC$^{low}$ Treg cells to the subject, wherein the immune and/or inflammatory disease or condition is selected from the group consisting of an autoimmune disease, graft rejection and GVHD.

2. The method of claim 1, wherein the population of immunosuppressive macrophages is allogeneic to the population of human PBMCs.

3. The method of claim 1, wherein the population of human monocytes is a population of CD14+ human monocytes.

4. The method of claim 1, wherein the IL-34 polypeptide is a human IL-34 polypeptide.

5. The method of claim 1, wherein the IL-34 polypeptide comprises or consists of SEQ ID NO: 1.

6. The method of claim 1, wherein the IL-34 polypeptide is added to the culture at a concentration ranging from 1 to 500 ng/mL.

7. The method of claim 1, wherein the IL-34 polypeptide is added to the culture at a concentration of 50 ng/mL.

8. The method of claim 1, wherein the co-culture of PBMCs and the population of immunosuppressive macrophages obtained at step (a) is performed in a medium comprising IL-15 and/or IL-2.

9. The method of claim 8, wherein the cytokines IL-15 and/or IL-2 are human IL-15 and/or human IL-2.

10. The method of claim 1, wherein the Treg cells are CD8+Foxp3+ CD45RC$^{low}$ Treg cells.

11. The method of claim 1, wherein the immune and/or inflammatory disease or condition is an autoimmune disease.

12. The method of claim 1, wherein the immune and/or inflammatory disease or condition is selected from the group consisting of graft rejection and GVHD.

\* \* \* \* \*

SEQUENCE LISTING

```
<160> NUMBER OF SEQ ID NOS: 1

<210> SEQ ID NO 1
<211> LENGTH: 242
<212> TYPE: PRT
<213> ORGANISM: Homo sapiens

<400> SEQUENCE: 1

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160
```

```
Pro Lys Ala Leu Leu Asp Asn Cys Phe Arg Val Met Glu Leu Leu Tyr
            165                 170                 175
Cys Ser Cys Cys Lys Gln Ser Ser Val Leu Asn Trp Gln Asp Cys Glu
            180                 185                 190
Val Pro Ser Pro Gln Ser Cys Ser Pro Glu Pro Ser Leu Gln Tyr Ala
        195                 200                 205
Ala Thr Gln Leu Tyr Pro Pro Pro Trp Ser Pro Ser Ser Pro Pro
        210                 215                 220
His Ser Thr Gly Ser Val Arg Pro Val Arg Ala Gln Gly Glu Gly Leu
225                 230                 235                 240
Leu Pro
```